(12) United States Patent
Ochiai

(10) Patent No.: US 8,551,744 B2
(45) Date of Patent: Oct. 8, 2013

(54) METHOD OF PREPARING A FATTY ACID COMPOSITION

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 409 days.

(21) Appl. No.: 12/668,513

(22) PCT Filed: Jul. 23, 2008

(86) PCT No.: PCT/JP2008/063191
§ 371 (c)(1),
(2), (4) Date: Jan. 11, 2010

(87) PCT Pub. No.: WO2009/014140
PCT Pub. Date: Jan. 29, 2009

(65) Prior Publication Data
US 2010/0323085 A1 Dec. 23, 2010

(30) Foreign Application Priority Data
Jul. 23, 2007 (JP) ................................. 2007-190680

(51) Int. Cl.
*C12P 7/64* (2006.01)

(52) U.S. Cl.
USPC ........................................................ 435/134

(58) Field of Classification Search
None
See application file for complete search history.

(56) References Cited

U.S. PATENT DOCUMENTS

| | | | |
|---|---|---|---|
| 2006/0051847 A1 | 3/2006 | Gunnarsson et al. | |
| 2006/0094090 A1 | 5/2006 | Damude et al. | |
| 2006/0174376 A1* | 8/2006 | Renz et al. | 800/281 |
| 2007/0072275 A1 | 3/2007 | Ochiai et al. | |

FOREIGN PATENT DOCUMENTS

| | | |
|---|---|---|
| JP | 8-205900 | 8/2006 |
| WO | 01/40514 | 6/2001 |
| WO | 2004/076617 | 9/2004 |
| WO | 2005/019437 | 3/2005 |
| WO | 2005/118814 | 12/2005 |

OTHER PUBLICATIONS

Issued_Patents_NA:* US2005/0174376 Renz et al, 2006 SEQ ID No. 16; alignment with SEQ ID No. 2.*
Anderson et al, A revised model of the active site of alternative oxidase. FEBS Lett. Apr. 16, 1999;449(1):17-22.*
Calder, "n-3 Fatty Acids, Inflammation, and Immunity-Relevance to Postsurgical and Critically Ill Patients," *Lipids*, vol. 39, pp. 1147-1161, 2004.
Coleman, "Characterization of the *Escherichia coli* Gene for 1-Acyl-*sn*-glycerol-3-phosphate Acyltransferase (*plsC*)," *Mol. Gen. Genet.*, vol. 232, pp. 295-303. 1992.
Nagiec et al., "A Suppressor Gene That Enables *Saccharomyces cerevisiae* to Grow Without Making Sphingolipids Encodes a Protein That Resembles an *Escherichia coli* Fatty Acyltransferase," *The Journal of Biological Chemistry*, vol. 268, No. 29, pp. 22156-22163, 1993.
Chatrattanakunchai et al., "Oil Biosynthesis in Microsomal Membrane Preparations from *Mortierella alpina*," *Biochemical Society Transactions*, vol. 28, part 6, pp. 707-709, 2000.
Heath et al., "A Conserved Histidine Is Essential for Glycerolipid Acyltransferase Catalysis," *J. Bacteriology*, vol. 180, No. 6, pp. 1425-1430, 1998.
Zinser et al., "Phospholipid Synthesis and Lipid Composition of Subcellular Membranes in the Unicellular Eukaryote *Saccharomyces cerevisiae*," *J. Bacteriology*, vol. 173, No. 6, pp. 2026-2034, 1991.
Coleman, "Characterization of *Escherichia coli* Cells Deficient in 1-Acyl-*sn*-glycerol-3-phosphate Acyltransferase Activity," *The Journal of Biological Chemistry*, vol. 265, No. 28, pp. 17215-17221, 1990.
Outcome Report of Consignment Research in 2004, along with an English-language translation thereof, May 2005.
International Search Report that issued with respect to PCT/JP2008/063191, mailed Aug. 26, 2008.
Beltran et al., "Influence of Harvest Date and Crop Yield on the Fatty Acid Composition of Virgin Olive Oils from Cv. Picual" *J. Agric. Food Chem.* 52(11):3434-40, 2004.
European Office Action issued with respect to EP Application No. 08 791 448.7, dated May 14, 2012.

* cited by examiner

*Primary Examiner* — Sheridan Swope
(74) *Attorney, Agent, or Firm* — Greenblum & Bernstein, P.L.C.

(57) ABSTRACT

The present invention provides a fatty acid composition obtained by culturing a host which is transformed with a recombinant vector comprising a nucleic acid of SEQ ID NO: 1 or a nucleic acid encoding a protein having the amino acid sequence shown in SEQ ID NO: 2 or a mutant functionally equivalent to the nucleic acid. The present invention also provides a method of making such a fatty acid composition.

6 Claims, 2 Drawing Sheets

```
                                                                        60
LPAAT1-long   MTVAKLDPGTTSPISPSASASFSPPTTPLSQKKGIYSATTTSTTTTTTTTTKISSSSNSS
LPAAT1-short  ------------------------------------------------------------
LPAAT1        ------------------------------------------------------------
              61                                                       120
LPAAT1-long   SATLMDESTTTTHHTETSSKTSSHPRRLGPKMNPIYKGLRAFVWALYFNLGASLISITQV
LPAAT1-short  ----MDESTTTTHHTETSSKTSSHPRRLGPKMNPIYKGLRAFVWALYFNLGASLISITQV
LPAAT1        ---MDESTTTTHHSETSSKTSSHPRRLGPEMNPIYKGLRAIVWAFYFNLGASLISITQV
              121                                                      180
LPAAT1-long   LSLPLALIAPKVYQWHITKTQGHFGAFLLKMNQLFAPSDIVLTGDESVRGIVKVYQGRRL
LPAAT1-short  LSLPLALIAPKVYQWHITKTQGHFGAFLLKMNQLFAPSDIVLTGDESVRGIVKVYQGRRL
LPAAT1        LSLPLALIAPGVYQWHISKTQGHFGAFLLRMNQLFAPSDIVLTGDESVRGIVKVYKGRNL
              181                                                      240
LPAAT1-long   KDTGEAYSGHGEDIILDMPERMVFIANHQIYSDWMYLWCFSYFAERHRALKIILRGDLTW
LPAAT1-short  KDTGEAYSGHGEDIILDMPERMVFIANHQIYSDWMYLWCFSYFAERHRALKIILRGDLTW
LPAAT1        KEAGEPGSGQGEDILLDMPERMVFIANHQIYSDWMYLWCFSYFAERHRALKIILRGDLTW
              241                                                      300
LPAAT1-long   IPVFGWGMRFFDFIFLKRNDWAHDRRAIEENLGRVKEKDPLWLVVFPEGTVVSKETRLRS
LPAAT1-short  IPVFGWGMRFFDFIFLKRNDWAHDRRAIEENLGRVKEKDPLWLVVFPEGTVVSKETRLRS
LPAAT1        IPVFGWGMRFFDFIFLKRNDWAHDRRAIEENLGRVKEKDPLWLVVFPEGTVVSKETRLRS
              301                                                      360
LPAAT1-long   VAFSKKAGLSDHRHVLLPRTSGLFVCINKLRGSVEYLYDATVGYSNVEYGEIPQELYPLP
LPAAT1-short  VAFSKKAGLSDHRHVLLPRTSGLFVCINKLRGSVEYLYDATVGYSNVEYGEIPQELYPLP
LPAAT1        VAFSKKASLSDHRHVLLPRTSGLFVCINKLRGSVDYLYDATVGYSNVEYGEIPQELYPLP
              361                                                      420
LPAAT1-long   GLYINKAQPKEINMHLRRFAIKDIPTSEPEFVEWVRARWVEKDELMEEFYTKGRFPSQLT
LPAAT1-short  GLYINKAQPKEINMHLRRFAIKDIPTSEPEFVEWVRARWVEKDELMEEFYTKGRFPSQLT
LPAAT1        GLYINKAQPKEINMHLRRFAIKDIPTSEPEFVEWVRARWVEKDELMEEFYTKGRFPSQLT
              421                                                      480
LPAAT1-long   AEDIGEKETNKAGGSSEGQSVRIPLKSRGMMDYLMPSAINLVALPVLAFAMRYALQQVSS
LPAAT1-short  AEDIGEKETNKAGGSSEGQSVRIPLKSRGMMDYLMPSAINLVALPVLAFAMRYALQQVSS
LPAAT1        AADIGEKEVKTAGGPTEGQSVRIPLKARGMMDYLMPSVMNLIALPVLAFAMRYAVQQASG
              481
LPAAT1-long   G
LPAAT1-short  G
LPAAT1        -
```

US 8,551,744 B2

METHOD OF PREPARING A FATTY ACID COMPOSITION

TECHNICAL FIELD

This specification claims priority to Japanese Patent Application No. 2007-190680 (filed on Jul. 23, 2007).

The present invention relates to a fatty acid composition obtained by culturing a host which is transformed with a recombinant vector carrying a nucleic acid comprising the nucleotide sequence of SEQ ID NO: 1 or a nucleotide sequence encoding a protein having the amino acid sequence shown in SEQ ID NO: 2 or a mutant functionally equivalent to the nucleic acid, wherein at least one or more of i) to v) shown below:

i) the oleic acid content;
ii) the ratio of the oleic acid content to the palmitic acid content;
iii) the ratio of the oleic acid content to the stearic acid content;
iv) the ratio of the total content of stearic acid and oleic acid to the total content of palmitic acid and palmitoleic acid; and
v) the n-6 fatty acid content is higher in the fatty acid rate of the fatty acid composition than in a cultured product obtained by culturing a host which is not transformed with the recombinant vector.

BACKGROUND ART

Fatty acids are important components of lipids such as phospholipids and triacylglycerols. Various physiological activities have been reported for polyunsaturated fatty acids (PUFA) containing two or more unsaturated bonds, including arachidonic acid, dihomo-γ-linolenic acid, eicosapentaenoic acid and docosahexaenoic acid (Non-patent Document 1). These polyunsaturated fatty acids are expected to have applications in various fields. To efficiently obtain these fatty acids, microbial techniques have been developed which involve culturing various microorganisms to obtain polyunsaturated fatty acids. Other attempts have also been made to produce polyunsaturated fatty acids in plants. In these cases, polyunsaturated fatty acids are known to be accumulated, for example, as components of storage lipids such as triacylglycerols within microorganism cells or plant seeds.

This triacylglycerol is produced in vivo starting from glycerol-3-phosphate via lysophosphatidic acid, phosphatidic acid and diacylglycerol.

As described above, the reaction in which lysophosphatidic acid (hereinafter also referred to as "LPA" or "1-acylglycerol-3-phosphate") is acylated to generate phosphatidic acid (hereinafter also referred to as "PA" or "1,2-diacyl-sn-glycerol-3-phosphate") is known to be mediated by lysophosphatidic acid acyltransferase (hereinafter also referred to as "LPAAT").

This LPAAT is also known as 1-acylglycerol-3-phosphate acyltransferase (E.C. 2.3.1.51). LPAAT genes have been reported so far in several organisms. As an LPAAT gene from *Escherichia coli*, the plsC gene has been cloned (Non-patent Document 2). In fungi, the SLC1 gene from *Saccharomyces cerevisiae* has been cloned (Non-patent Document 3). Likewise, LPAAT genes have also been cloned from animals and plants (Patent Document 1).

For the LPAAT gene from a lipid-producing fungus, *Mortierella alpina* (hereinafter also referred to as "*M. alpina*"), two homologs have been reported (Patent Documents 2 and 3).

Patent Document 2 discloses cloning of a *M. alpine*-derived LPAAT homolog (LPAAT1), which is a gene having a CDS of 1254 nucleotides and consisting of the nucleotide sequence shown in SEQ ID NO: 16. This document also reports that when this LPAAT1 was co-expressed in yeast cells with Δ6 desaturase and Δ6 elongase and cultured in a medium supplemented with specific fatty acids, such yeast cells produced larger amounts of fatty acids whose chain length is longer and/or whose unsaturation degree is higher than that of the supplemented fatty acids, when compared to strains not expressing LPAAT1 (Patent Document 2).

Patent Document 1: International Patent Publication No. WO2004/076617
Patent Document 2: US Patent Publication No. 2006/174376
Patent Document 3: US Patent Publication No. 2006/0094090
Non-patent Document 1: Lipids, 39, 1147 (2004)
Non-patent Document 2: Mol. Gen. Genet., 232, 295-303, 1992
Non-patent Document 3: J.B.C., 268, 22156-22163, 1993
Non-patent Document 4: Biochemical Society Transactions, 28, 707-709, 2000
Non-patent Document 5: J. Bacteriology, 180, 1425-1430, 1998
Non-patent Document 6: J. Bacteriology, 173, 2026-2034 1991

DISCLOSURE OF THE INVENTION

Problems to be Solved by the Invention

However, even if LPAAT genes previously reported are introduced into and expressed in host cells, fatty acid compositions produced by the hosts are limited due to the substrate specificity of the expressed enzymes. For this reason, there is a need to identify a gene which allows production of a fatty acid composition whose fatty acid rate differs from that previously reported.

Means for Solving the Problems

The object of the present invention is to provide a fatty acid composition having a fatty acid rate useful for preparing fats and oils or food products, etc.

To achieve the above object, the inventors of the present invention have made extensive and intensive efforts. First, a gene called LPAAT1-long, which is derived from a lipid-producing fungus, *Mortierella alpina*, was isolated and introduced into highly proliferative host cells (e.g., yeast cells) to thereby produce a fatty acid composition. As a result, the inventors succeeded in producing a fatty acid composition different from those obtained by known LPAATs. This led to the completion of the present invention. Namely, the present invention is as follows.

(1) A fatty acid composition obtained by culturing a host which is transformed with a recombinant vector carrying a nucleic acid comprising a nucleotide sequence shown in any one of (a) to (e) below:

(a) a nucleotide sequence which encodes a protein consisting of an amino acid sequence with deletion, substitution or addition of one or more amino acids in the amino acid sequence shown in SEQ ID NO: 2 and having lysophosphatidic acid acyltransferase activity;

(b) a nucleotide sequence which is hybridizable under high stringent conditions with a nucleic acid consisting of a nucleotide sequence complementary to a nucleotide sequence consisting of SEQ ID NO: 1 and which encodes a protein having lysophosphatidic acid acyltransferase activity;

(c) a nucleotide sequence which consists of a nucleotide sequence sharing an identity of 90% or more with a nucleotide sequence consisting of SEQ ID NO: 1 and which encodes a protein having lysophosphatidic acid acyltransferase activity;

(d) a nucleotide sequence which encodes an amino acid sequence sharing an identity of 90% or more with an amino acid sequence consisting of SEQ ID NO: 2 and which encodes a protein having lysophosphatidic acid acyltransferase activity; or (e) a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having lysophosphatidic acid acyltransferase activity, wherein at least one or more of i) to v) shown below is higher in the fatty acid rate of the fatty acid composition than in a cultured product obtained by culturing a host which is not transformed with the recombinant vector:
  i) the oleic acid content;
  ii) the ratio of the oleic acid content to the palmitic acid content;
  iii) the ratio of the oleic acid content to the stearic acid content;
  iv) the ratio of the total content of stearic acid and oleic acid to the total content of palmitic acid and palmitoleic acid; and
  v) the n-6 fatty acid content.

Alternatively, the fatty acid composition of the present invention may also be a fatty acid composition obtained by culturing a host which is transformed with a recombinant vector carrying a nucleic acid comprising a nucleotide sequence shown in any one of (a) to (e) below:

(a) a nucleotide sequence which encodes an amino acid sequence with deletion, substitution or addition of one or more amino acids in the amino acid sequence shown in SEQ ID NO: 2;

(b) a nucleotide sequence which is hybridizable under high stringent conditions with a nucleic acid consisting of a nucleotide sequence complementary to a nucleotide sequence consisting of SEQ ID NO: 1;

(c) a nucleotide sequence which consists of a nucleotide sequence sharing an identity of 90% or more with a nucleotide sequence consisting of SEQ ID NO: 1;

(d) a nucleotide sequence which encodes an amino acid sequence sharing an identity of 90% or more with an amino acid sequence consisting of SEQ ID NO: 2; or (e) a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2.

(2) The fatty acid composition according to (1) above, wherein the nucleic acid comprises a nucleotide sequence shown in any one of (a) to (c) below:

(a) a nucleotide sequence which encodes a protein consisting of an amino acid sequence with deletion, substitution or addition of 1 to 10 amino acids in the amino acid sequence shown in SEQ ID NO: 2 and having lysophosphatidic acid acyltransferase activity;

(b) a nucleotide sequence which is hybridizable under conditions of 1×SSC at 60° C. with a nucleic acid consisting of a nucleotide sequence complementary to a nucleotide sequence consisting of SEQ ID NO: 1 and which encodes a protein having lysophosphatidic acid acyltransferase activity; or (c) a nucleotide sequence which encodes an amino acid sequence sharing an identity of 95% or more with an amino acid sequence consisting of SEQ ID NO: 2 and which encodes a protein having lysophosphatidic acid acyltransferase activity.

(3) The fatty acid composition according to (1) above, wherein the nucleic acid comprises a nucleotide sequence shown in (a) or (b) below:
  (a) the nucleotide sequence shown in SEQ ID NO: 1; or
  (b) a nucleotide sequence encoding a protein consisting of the amino acid sequence shown in SEQ ID NO: 2.

(4) The fatty acid composition according to (1) above, wherein the n-6 fatty acid is at least one fatty acid selected from the group consisting of linolic acid, γ-linolenic acid, dihomo-γ-linolenic acid (DGLA) and arachidonic acid.

5) A method for preparing a fatty acid composition, which comprises collecting a fatty acid composition from a cultured product obtained by culturing a host which is transformed with a recombinant vector carrying a nucleic acid comprising a nucleotide sequence shown in any one of (a) to (e) below:

(a) a nucleotide sequence which encodes a protein consisting of an amino acid sequence with deletion, substitution or addition of one or more amino acids in the amino acid sequence shown in SEQ ID NO: 2 and having lysophosphatidic acid acyltransferase activity;

(b) a nucleotide sequence which is hybridizable under high stringent conditions with a nucleic acid consisting of a nucleotide sequence complementary to a nucleotide sequence consisting of SEQ ID NO: 1 and which encodes a protein having lysophosphatidic acid acyltransferase activity;

(c) a nucleotide sequence which consists of a nucleotide sequence sharing an identity of 90% or more with a nucleotide sequence consisting of SEQ ID NO: 1 and which encodes a protein having lysophosphatidic acid acyltransferase activity;

(d) a nucleotide sequence which encodes an amino acid sequence sharing an identity of 90% or more with an amino acid sequence consisting of SEQ ID NO: 2 and which encodes a protein having lysophosphatidic acid acyltransferase activity; or (e) a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having lysophosphatidic acid acyltransferase activity, wherein the fatty acid composition has a higher value for at least one or more of i) to v) shown below in comparison with a cultured product obtained by culturing a host which is not transformed with the recombinant vector:
  i) the oleic acid content;
  ii) the ratio of the oleic acid content to the palmitic acid content;
  iii) the ratio of the oleic acid content to the stearic acid content;
  iv) the ratio of the total content of stearic acid and oleic acid to the total content of palmitic acid and palmitoleic acid; and
  v) the n-6 fatty acid content.

(6) The method according to (5) above, wherein the n-6 fatty acid is at least one fatty acid selected from the group consisting of linolic acid, γ-linolenic acid, dihomo-γ-linolenic acid and arachidonic acid.

(7) The method according to (5) or (6) above, wherein the nucleic acid comprises a nucleotide sequence shown in any one of (a) to (c) below:

(a) a nucleotide sequence which encodes a protein consisting of an amino acid sequence with deletion, substitution or addition of 1 to 10 amino acids in the amino acid sequence shown in SEQ ID NO: 2 and having lysophosphatidic acid acyltransferase activity;

(b) a nucleotide sequence which is hybridizable under conditions of 1×SSC at 60° C. with a nucleic acid consisting of a nucleotide sequence complementary to a nucleotide sequence consisting of SEQ ID NO: 1 and which encodes a protein having lysophosphatidic acid acyltransferase activity; or (c) a nucleotide sequence which encodes an amino acid sequence sharing an identity of 95% or more with an amino acid sequence consisting of SEQ ID NO: 2 and which encodes a protein having lysophosphatidic acid acyltransferase activity.

(8) Use of a nucleic acid comprising a nucleotide sequence shown in any one of (a) to (e) below for the manufacture of the fatty acid composition according to any one of (1) to (4) above:

(a) a nucleotide sequence which encodes a protein consisting of an amino acid sequence with deletion, substitution or addition of one or more amino acids in the amino acid sequence shown in SEQ ID NO: 2 and having lysophosphatidic acid acyltransferase activity;

(b) a nucleotide sequence which is hybridizable under high stringent conditions with a nucleic acid consisting of a nucleotide sequence complementary to a nucleotide sequence consisting of SEQ ID NO: 1 and which encodes a protein having lysophosphatidic acid acyltransferase activity;

(c) a nucleotide sequence which consists of a nucleotide sequence sharing an identity of 90% or more with a nucleotide sequence consisting of SEQ ID NO: 1 and which encodes a protein having lysophosphatidic acid acyltransferase activity;

(d) a nucleotide sequence which encodes an amino acid sequence sharing an identity of 90% or more with an amino acid sequence consisting of SEQ ID NO: 2 and which encodes a protein having lysophosphatidic acid acyltransferase activity; or (e) a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having lysophosphatidic acid acyltransferase activity.

(9) The use according to (8) above, wherein the nucleic acid comprises a nucleotide sequence shown in any one of (a) to (c) below:

(a) a nucleotide sequence which encodes a protein consisting of an amino acid sequence with deletion, substitution or addition of 1 to 10 amino acids in the amino acid sequence shown in SEQ ID NO: 2 and having lysophosphatidic acid acyltransferase activity;

(b) a nucleotide sequence which is hybridizable under conditions of 1×SSC at 60° C. with a nucleic acid consisting of a nucleotide sequence complementary to a nucleotide sequence consisting of SEQ ID NO: 1 and which encodes a protein having lysophosphatidic acid acyltransferase activity; or (c) a nucleotide sequence which encodes an amino acid sequence sharing an identity of 95% or more with an amino acid sequence consisting of SEQ ID NO: 2 and which encodes a protein having lysophosphatidic acid acyltransferase activity.

(10) A food product comprising the fatty acid composition according to any one of (1) to (4) above.

Advantages of the Invention

LPAAT1-long of the present invention has substrate specificity different from that of known LPAAT1, and allows a host to produce a fatty acid composition whose fatty acid rate differs from that of a fatty acid composition produced by a host expressing known LPAAT1. As a result, LPAAT1-long of the present invention enables the provision of lipids having desired properties and effects, and is useful as being applicable to foods, cosmetics, pharmaceuticals, soaps, etc.

The arachidonic acid content in host cells expressing LPAAT1-long of the present invention is higher than that of host cells not expressing LPAAT1-long of the present invention. A fatty acid composition obtained from a cultured product of these LPAAT1-long-expressing cells is expected to provide a nutritionally higher effect and hence is preferred.

Moreover, the LPAAT of the present invention allows improvement in the ability to produce fatty acids and storage lipids, and hence is preferred as a means for improving the productivity of polyunsaturated fatty acids in microorganisms and plants.

BRIEF DESCRIPTION OF THE DRAWINGS

FIG. 1 shows a comparison of LPAAT1-long (SEQ ID NO: 4) and LPAAT1-short (SEQ ID NO: 30) in the present invention with LPAAT1 (SEQ ID NO: 31) for their CDS nucleotide sequences.

FIG. 2 shows a comparison of LPAAT1-long (SEQ ID NO: 2) and LPAAT1-short (SEQ ID N: 10) in the present invention with LPAAT1 (SEQ ID NO: 32) for their CDS amino acid sequences.

BEST MODE FOR CARRYING OUT THE INVENTION

The present invention relates to a novel fatty acid composition, a method for preparing the fatty acid composition, and a food product comprising the fatty acid composition.

The present invention will be explained in more detail below.

The present invention uses a lysophosphatidic acid acyltransferase (LPAAT) gene from the genus *Mortierella*, which is characterized by allowing production of the above novel fatty acid composition. More specifically, the present invention uses a nucleic acid referred to as LPAAT1-long or a mutant thereof, which was isolated by the inventors and is shown in SEQ ID NO: 1. It should be noted that lysophosphatidic acid acyltransferase is an enzyme that catalyzes a reaction in which lysophosphatidic acid is acylated to generate phosphatidic acid. The term "LPAAT1-long" or "LPAAT1-short" is used herein to describe a strain, a gene, a protein, or alternatively, a cell obtained by culturing a transformant which is created by inserting the above LPAAT1-long or LPAAT1-short gene into an expression vector and transforming the vector into an appropriate host.

Homologs of Lysophosphatidic Acid Acyltransferase (LPAAT) 1

Sequences related to LPAAT1-long of the present invention include SEQ ID NO: 1 (sequence representing the ORF region of LPAAT1-long), SEQ ID NO: 2 (amino acid sequence of LPAAT1-long), SEQ ID NO: 3 (nucleotide sequence of cDNA for LPAAT1-long) and SEQ ID NO: 4 (sequence representing the CDS region of LPAAT1-long). Among them, SEQ ID NO: 1 corresponds to nucleotides 115-1557 of SEQ ID NO: 3.

In addition to LPAAT1-long, the inventors of the present invention have isolated another LPAAT1 gene (hereinafter also referred to as "LPAAT1-short") which corresponds to 86.8% of the entire nucleotide sequence of LPAAT1-long and 86.7% of the entire amino acid sequence of LPAAT1-long.

Sequences related to LPAAT1-short include SEQ ID NO: 8 (sequence representing the ORF region of LPAAT1-short), SEQ ID NO: 10 (amino acid sequence of LPAAT1-short) and SEQ ID NO: 9 (nucleotide sequence of cDNA for LPAAT1-short). Nucleotides 36-1286 of SEQ ID NO: 9 correspond to ORF shown in SEQ ID NO: 8. The relationship between LPAAT1-long and LPAAT1-short is as shown in Table 1 below.

TABLE 1

Relationship of LPAAT1 homologs

|  | LPAAT1-long | LPAAT1-short | LPAAT1 (Patent Document 2) |
|---|---|---|---|
| Nucleotide sequence | SEQ ID NO: 1 | SEQ ID NO: 8 | SEQ ID NO: 16 (Patent Document 2) |
| Number of nucleotides in ORF | 1443 | 1251 | 1251 |
| Corresponding position in SEQ ID NO: 1 | *** | 193-1443 | 193-1443 |
| Percentage (length) relative to SEQ ID NO: 1 | *** | 86.8% | 86.8% |
| Amino acid sequence | SEQ ID NO: 2 | SEQ ID NO: 10 | SEQ ID NO: 10 (Patent Document 2) |
| Number of amino acid residues | 481 | 417 | 417 |
| Corresponding position in SEQ ID NO: 2 | *** | 65-481 | 65-481 |
| Percentage relative to SEQ ID NO: 2 | *** | 86.70% | 86.70% |

Namely, a nucleotide sequence with 5'-terminal deletion in the ORF nucleotide sequence of LPAAT1-long of the present invention corresponds to LPAAT1-short. In detail, among 1443 nucleotides in the ORF nucleotide sequence (SEQ ID NO: 1) of LPAAT1-long of the present invention, nucleotides in a region between positions 193 and 1443, which constitute 86.8% of the total nucleotides, correspond to the ORF nucleotide sequence (SEQ ID NO: 8) of LPAAT1-short. Namely, LPAAT1-long is a sequence longer than LPAAT1-short by 192 nucleotides in the 5'-region. Likewise, among 481 residues in the amino acid sequence (SEQ ID NO: 2) of LPAAT1-long of the present invention, residues in a region between positions 65 and 481, which constitute 86.7% of the total residues, correspond to the amino acid sequence (SEQ ID NO: 8) of LPAAT1-short. Namely, LPAAT1-long is a sequence longer than LPAAT1-short by 64 amino acid residues (amino acid residues 1-64 in SEQ ID NO: 2) at the N-terminal end.

Figure 1:
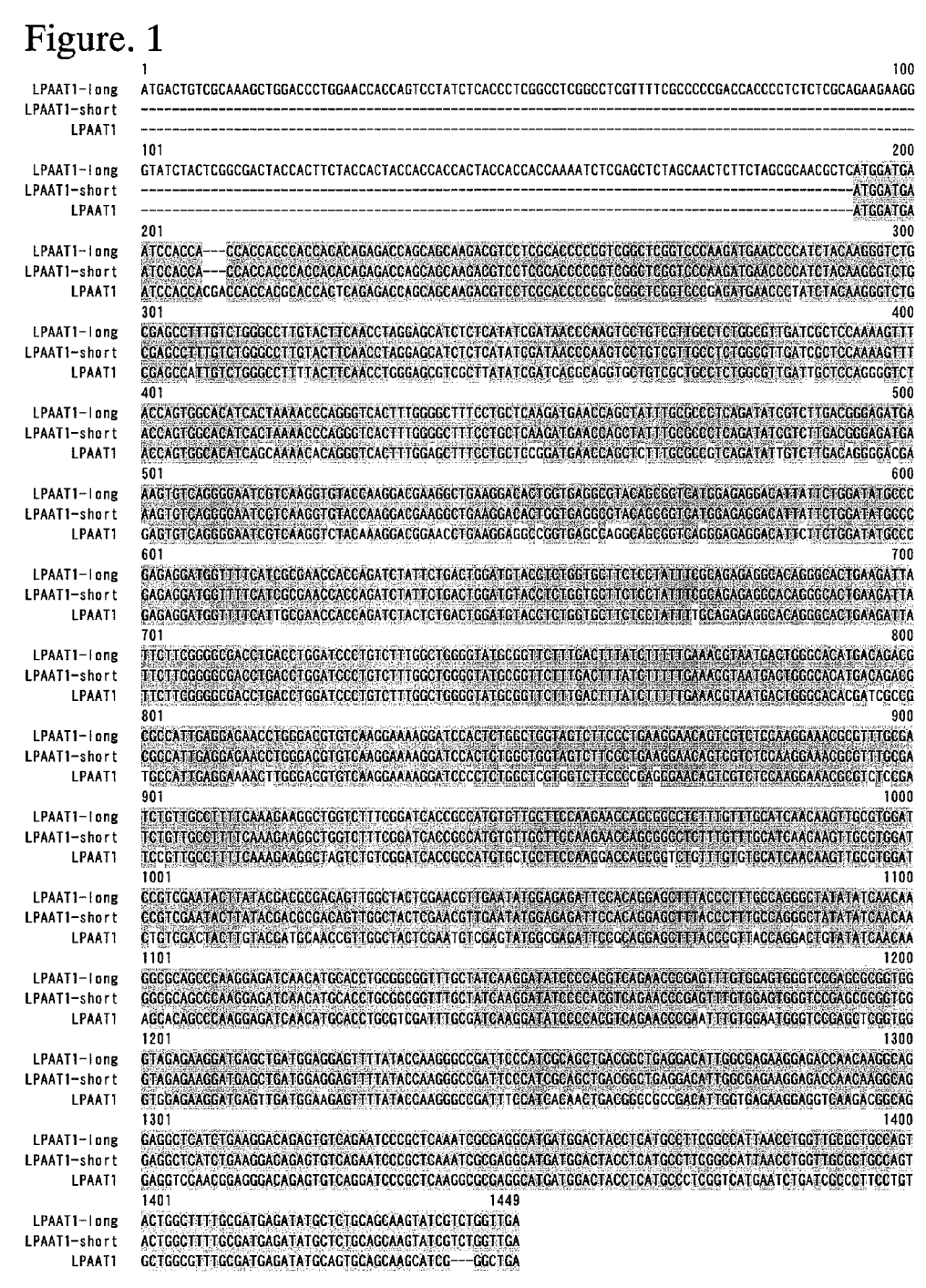

It should be noted that known LPAAT derived from *M. alpina* (hereinafter referred to as "LPAAT1") is disclosed in Patent Document 2 listed above. The number of nucleotides in ORF of this LPAAT1 is 1251, which is identical to that of LPAAT1-short. The nucleotide sequence identity between these ORFs is as high as 89%, suggesting that LPAAT1-short would be an isoallele of LPAAT1. FIGS. 1 and 2 show nucleotide and amino acid sequence alignments, respectively, for LPAAT1-long, LPAAT1-short and LPAAT1 (FIGS. 1 and 2).

Thus, the inventors used LPAAT1-short as a model of known LPAAT1 for comparison purposes in studying the activity of LPAAT1-long of the present invention. More specifically, LPAAT1-long and LPAAT1-short were expressed in yeast cells and the resulting fatty acid compositions were compared for their fatty acid rate. As a result, as explained in detail below, the fatty acid rate of a fatty acid composition produced by a host expressing the LPAAT1-long gene of the present invention was completely different from that of a fatty acid composition produced by a host expressing LPAAT1-short. Namely, LPAAT1-long of the present invention was found to have the ability to produce a fatty acid composition whose fatty acid rate is completely different from that of a fatty acid composition produced by known LPAAT1.

More specifically, one of the characteristic features in the fatty acid composition of the present invention is high arachidonic acid content. Arachidonic acid, a substance represented by the chemical formula $C_{20}H_{32}O_2$ and having a molecular weight of 304.47, is a carboxylic acid containing 20 carbon atoms and 4 double bonds ([20:4(n-6)]) and classified as a member of the (n-6) series. Arachidonic acid is present as an important phospholipid (particularly phosphatidylethanolamine, phosphatidylcholine, phosphatidylinositol) in animal cell membranes and is contained in abundance in the brain. Moreover, arachidonic acid serves as a starting material for a series of eicosanoids (e.g., prostaglandin, thromboxane, leukotriene) generated by the arachidonic acid cascade, and is also important as a second messenger in intercellular signaling. On the other hand, arachidonic acid is synthesized from linolic acid in the animal body. However, depending on their species or age, some animals do not exert this function sufficiently to produce the required amount of arachidonic acid or have no function to produce arachidonic acid. Thus, arachidonic acid should be taken from food sources and can be regarded as an essential fatty acid.

The arachidonic acid content in the fatty acid composition of the present invention may be measured as follows, by way of example. Namely, a plasmid for LPAAT1-long of the present invention is inserted into a vector such as pDuraSC or pDura5MCS, as described in Examples 8 and 9, and transformed into a *M. alpina* strain. The resulting transformant is allowed to express and cultured according to the procedures described in Example 10. The cultured cells thus obtained are used to measure the fatty acid rate and/or arachidonic acid content in the cells, etc. To analyze the arachidonic acid content, etc., for example, fatty acids in the resulting cultured cells are derived into corresponding fatty acid methyl esters by the hydrochloric acid/methanol method, and then extracted with hexane. After distilling off hexane, the fatty acids are analyzed by gas chromatography. According to this analysis, *M. alpina* transformed with LPAAT1-long of the present invention has been found to show a high content of arachidonic acid among fatty acids in the cells. Thus, the fatty acid composition of the present invention having high arachidonic acid content is preferred because it enables the efficient intake of arachidonic acid.

As shown above, LPAAT1-long of the present invention has activity that is completely different from that of known LPAAT1. One of the grounds for such novel activity may be a difference in gene/protein structure between LPAAT1-long of the present invention and known LPAAT1. Thus, mutants having a nucleotide sequence/amino acid sequence extremely close to that of LPAAT1-long of the present invention and being functionally equivalent to LPAAT1-long also fall within the scope of the present invention. Examples include the following:

i) those whose nucleotide sequence/amino acid sequence is about 90% identical to that of the specific LPAAT1-long of the present invention (around 144 nucleotides or around 48 amino acid residues are identical; also including mutants with deletion, substitution or addition of these nucleotides/residues); and ii) those whose nucleotide sequence/amino acid sequence is hybridizable under high stringent conditions with that of LPAAT1-long of the present invention.

Details are as given in the section "Nucleic acids of the present invention encoding lysophosphatidic acid acyltransferase" described below.

Nucleic Acids of the Present Invention Encoding Lysophosphatidic Acid Acyltransferase (LPAAT)

The present invention relates to a fatty acid composition having a novel fatty acid rate, obtained by culturing a host which is transformed with a recombinant vector carrying a nucleic acid comprising the nucleotide sequence of SEQ ID NO: 1 (LPAAT1-long) or the like, as well as a method for preparing the same. First, an explanation will be given of nucleic acids used for preparing the above fatty acid composition.

As described above, lysophosphatidic acid acyltransferase (LPAAT) in the present invention encompasses LPAAT1-long. Sequences related to LPAAT1-long of the present invention include SEQ ID NO: 1 (sequence representing the ORF region of LPAAT1-long), SEQ ID NO: 2 (amino acid sequence of LPAAT1-long), SEQ ID NO: 3 (nucleotide sequence of cDNA for LPAAT1-long) and SEQ ID NO: 4 (sequence representing the CDS region of LPAAT1-long), as explained in the section "Homologs of lysophosphatidic acid acyltransferase (LPAAT) 1."

The nucleic acids of the present invention encompass single-stranded and double-stranded DNAs as well as complementary RNAs thereof, which may be either naturally occurring or artificially prepared. DNAs include, but are not limited to, genomic DNAs, cDNAs corresponding to the genomic DNAs, chemically synthesized DNAs, PCR-amplified DNAs, as well as combinations thereof and DNA/RNA hybrids.

Preferred embodiments for the nucleic acids of the present invention include (a) the nucleotide sequence shown in SEQ ID NO: 1, and (b) a nucleotide sequence encoding a protein consisting of the amino acid sequence shown in SEQ ID NO: 2.

To obtain these nucleotide sequences, nucleotide sequence data of ESTs or genomic DNAs from organisms having LPAAT activity may be used to search a nucleotide sequence encoding a protein sharing high identity with known proteins having LPAAT activity. Preferred organisms having LPAAT activity are lipid-producing fungi including, but not limited to, *M. alpina*.

For EST analysis, a cDNA library is first prepared. As to techniques for cDNA library preparation, reference may be made to "Molecular Cloning, A Laboratory Manual 3rd ed." (Cold Spring Harbor Press (2001)). Alternatively, a commercially available cDNA library preparation kit may be used. Techniques for cDNA library preparation suitable for the present invention are as follows, by way of example. Namely, an appropriate strain of *M. alpina*, a lipid-producing fungus, is inoculated into an appropriate medium and pre-cultured for an appropriate period. Culture conditions suitable for this pre-culture include, for example, medium composition of 1.8% glucose, 1% yeast extract and pH 6.0, a culture period of 3 days, and a culture temperature of 28° C. The pre-cultured product is then subjected to main culture under appropriate conditions. Medium composition suitable for main culture may be, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$ and pH 6.0. Culture conditions suitable for main culture may be, for example, aerobic spinner culture at 300 rpm, 1 vvm, 26° C. for 8 days. An appropriate amount of glucose may be added during culture. The cultured product is sampled at appropriate time points during main culture, from which the cells are then collected to prepare total RNA. For preparation of total RNA, it is possible to use any known technique, such as guanidine hydrochloride/CsCl method. The resulting total RNA may be treated with a commercially available kit to purify poly(A) $^+$RNA. Further, a cDNA library may be prepared with a commercially available kit. Then, any clone from the cDNA library thus prepared is determined for its nucleotide sequence by using primers which are designed on a vector to allow determination of the nucleotide sequence of an insert. As a result, ESTs can be obtained. For example, when a ZAP-cDNA GigapackIII Gold Cloning Kit (STRATAGENE) is used for cDNA library preparation, directional cloning can be performed.

The present invention also encompasses nucleic acids functionally equivalent to a nucleic acid comprising the above nucleotide sequence shown in SEQ ID NO: 1 (hereinafter also referred to as "the nucleotide sequence of the present invention") or nucleotide sequence encoding a protein consisting of the amino acid sequence shown in SEQ ID NO: 2 (hereinafter also referred to as "the amino acid sequence of the present invention"). The phrase "functionally equivalent" is intended to mean that a protein encoded by the nucleotide sequence of the present invention or a protein consisting of the amino acid sequence of the present invention has LPAAT activity. In addition to this LPAAT activity, a protein encoded by the nucleotide sequence of the present invention or a protein consisting of the amino acid sequence of the present invention may have the ability to yield a fatty acid rate ensuring a higher value for at least one or more of:

i) the oleic acid content;
ii) the ratio of the oleic acid content to the palmitic acid content;
iii) the ratio of the oleic acid content to the stearic acid content;
iv) the ratio of the total content of stearic acid and oleic acid to the total content of palmitic acid and palmitoleic acid; and
v) the n-6 fatty acid content in the fatty acid rate of a host expressing the protein than in the fatty acid rate of a host not expressing the protein (such a protein is hereinafter also referred to as a "protein having the ability to yield the fatty acid rate of LPAAT in the present invention").

A specific example is a nucleic acid comprising a nucleotide sequence encoding a protein having the ability to yield a fatty acid rate ensuring the following:

i) the oleic acid content is 47% or more;
ii) the ratio of the oleic acid content to the palmitic acid content is 6.7 or more;
iii) the ratio of the oleic acid content to the stearic acid content is 10 or more; and/or
iv) the ratio of the total content of stearic acid and oleic acid to the total content of palmitic acid and palmitoleic acid is 1.1 or more, when the above nucleotide sequence of the present invention is inserted into expression vector pYE22m (Biosci. Biotech. Biochem., 59, 1221-1228, 1995) and transformed into a yeast host, *Saccharomyces cerevisiae* strain EH13-15 (Appl. Microbiol. Biotechnol., 30, 515-520, 1989), and the resulting transformant is cultured to collect the cells, which are then analyzed for fatty acids by the procedures described in Example 6 below. More preferred is a nucleic acid comprising a nucleotide sequence encoding a protein having both LPAAT activity and the above ability to yield the fatty acid rate of LPAAT in the present invention.

As a result of fatty acid analysis on LPAAT1-long of the present invention and LPAAT1-short as described in Example 6, LPAAT1-long of the present invention achieved an oleic acid content of around 54%, which was higher than that of LPAAT1-short (around 42%), as shown in Table 3 below. Moreover, the palmitic acid content in the present invention was around 7.6%, which was equal to that of the control and lower than that of LPAAT1-short (around 13.5%). Further, LPAAT1-long of the present invention resulted in a 1.8- to 2.5-fold higher ratio of the oleic acid content to the palmitic acid content than LPAAT1-short. Likewise, LPAAT1-long of the present invention resulted in about a 1.5- to 1.8-fold higher ratio of the oleic acid content to the stearic acid content than LPAAT1-short.

Furthermore, a protein encoded by the nucleotide sequence of the present invention or a protein consisting of the amino acid sequence of the present invention may also have the ability to yield a fatty acid rate ensuring a higher n-6 fatty acid content in the fatty acid rate of a host expressing the protein than in the fatty acid rate of a host not expressing the protein (such a protein is hereinafter also referred to as a "protein having the ability to yield the fatty acid rate of LPAAT in the present invention" as in the case above). N-6 fatty acids include, but are not limited to, linolic acid, γ-linolenic acid, dihomo-γ-linolenic acid, arachidonic acid, 7,10,13,16-docosatetraenoic acid and 4,7,10,13,16-docosapentaenoic acid. For example, n-6 fatty acids preferred for *M. alpina* include linolic acid, γ-linolenic acid, dihomo-γ-linolenic acid and arachidonic acid.

A specific example is a nucleic acid comprising a nucleotide sequence encoding a protein ensuring a higher n-6 fatty acid content, as shown for LPAAT1-long of the present invention in Table 5 below, when the above nucleotide sequence of the present invention is inserted into expression vector pYE22m and transformed into an arachidonic acid-producible yeast or filamentous fungal host (e.g., *Saccharomyces cerevisiae* or *Mortierella* strains bred to allow arachidonic acid production), and the resulting transformant is cultured to collect the cells, which are then analyzed for fatty acids by the procedures described in Examples 7-10 below.

In a case where LPAAT1-long of the present invention or LPAAT1-short was expressed in a yeast strain bred to allow arachidonic acid production, the results of fatty acid analysis performed by the procedures described in Example 7 are as shown in Table 4 below. Namely, LPAAT1-long of the present invention results in a higher linolic acid content than the control and LPAAT1-short. Likewise, LPAAT1-long of the present invention also results in a higher γ-linolenic acid content than the control and LPAAT1-short. Moreover, LPAAT1-long of the present invention results in a DGLA content which is higher than that of the control and is equal to that of LPAAT1-short. Furthermore, LPAAT1-long of the present invention results in a higher arachidonic acid content than the control and LPAAT1-short.

In a case where LPAAT1-long of the present invention or LPAAT1-short was expressed in *M. alpina*, the results of fatty acid analysis performed by the procedures described in Examples 8-10 are as shown in Table 5 below. Namely, LPAAT1-long of the present invention results in higher arachidonic acid and DGLA contents than the control and LPAAT1-short.

Thus, as will be explained later, LPAAT1-long of the present invention has a completely new function which cannot be expected from the prior art, because it allows a host to produce a fatty acid composition whose fatty acid rate is completely different from that of fatty acid compositions produced by hosts expressing other LPAATs.

Such nucleic acids that are functionally equivalent to the nucleic acids of the present invention include a nucleic acid comprising a nucleotide sequence shown in any one of (a) to (e) below (hereinafter also referred to as "the (functionally equivalent) mutant of the present invention"). It should be noted that when used to describe the nucleotide sequences listed below, the phrase "the above activity of the present invention" is intended to mean "LPAAT activity and/or the ability to yield the fatty acid rate of LPAAT in the present invention" defined above.

(a) A nucleotide sequence which encodes a protein consisting of an amino acid sequence with deletion, substitution or addition of one or more amino acids in the amino acid sequence shown in SEQ ID NO: 2 and having the above activity of the present invention.

Nucleotide sequences contained in the nucleic acids of the present invention include a nucleotide sequence which encodes a protein consisting of an amino acid sequence with deletion, substitution or addition of one or more amino acids in the amino acid sequence shown in SEQ ID NO: 2 and having the above activity of the present invention.

More specifically, as explained in the section "Homologs of lysophosphatidic acid acyltransferase (LPAAT) 1," it is a nucleotide sequence which encodes a protein consisting of:

(i) an amino acid sequence with deletion of one or more (preferably one or several (e.g., 1-48, 1-32, 1-24, 1-20, 1-16, 1-12, 1-10, 1-8, more preferably 1-4)) amino acids in the amino acid sequence shown in SEQ ID NO: 2;

(ii) an amino acid sequence with substitution of other amino acids for one or more (preferably one or several (e.g., 1-48, 1-32, 1-24, 1-20, 1-16, 1-12, 1-10, 1-8, more preferably 1-4)) amino acids in the amino acid sequence shown in SEQ ID NO: 2;

(iii) an amino acid sequence with addition of other one or more (preferably one or several (e.g., 1-48, 1-32, 1-24, 1-20, 1-16, 1-12, 1-10, 1-8, more preferably 1-4)) amino acids in the amino acid sequence shown in SEQ ID NO: 2; or (iv) an amino acid sequence with any combination of (i) to (iii) above, and having the above activity of the present invention.

Among the above modifications, substitution is preferably conservative, which means the replacement of a certain amino acid residue by another residue having similar physical and chemical characteristics. It may be any substitution as long as it does not substantially alter the structural characteristics of the original sequence. For example, any substitution is possible as long as the substituted amino acids do not disrupt a helix present in the original sequence or do not disrupt any other type of secondary structure characterizing the original sequence.

Conservative substitution is generally introduced by synthesis in biological systems or chemical peptide synthesis, preferably by chemical peptide synthesis. In this case, substituents may include unnatural amino acid residues, as well as peptidomimetics, and reversed or inverted forms of amino acid sequences in which unsubstituted regions are reversed or inverted.

Amino acid residues are classified and listed below in groups of mutually substitutable members, but are not limited to the following:

Group A: leucine, isoleucine, norleucine, valine, norvaline, alanine, 2-aminobutanoic acid, methionine, O-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and

Group G: phenylalanine and tyrosine.

Non-conservative substitution may involve the exchange of a member of one of the above classes for a member from another class. In this case, for the purpose of maintaining biological functions of the proteins of the present invention, it is preferable to consider the hydropathic index of amino acids (hydropathic amino acid index) (Kyte et al., J. Mol. Biol., 157:105-131 (1982)).

In the case of non-conservative substitution, amino acid substitutions may also be accomplished on the basis of hydrophilicity.

In the specification and drawings of the present application, nucleotides, amino acids and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomer, unless otherwise specified.

Stereoisomers (e.g., D-amino acids) of the above amino acids, unnatural amino acids such as $\alpha,\alpha$-disubstituted amino acids, N-alkylamino acids, lactic acid, and other unconventional amino acids may also be members constituting the proteins of the present invention.

It should be noted that in the protein notation used herein, the lefthand direction is the amino terminal direction and the righthand direction is the carboxy terminal direction, in accordance with standard usage and convention.

Similarly, unless otherwise specified, the lefthand end of single-stranded polynucleotide sequences is the 5'-end and the lefthand direction of double-stranded polynucleotide sequences is referred to as the 5' direction.

Those skilled in the art would be able to design and prepare appropriate mutants of the proteins described herein by using techniques known in the art. For example, when targeting a region which appears to be less important for the biological activity of the protein of the present invention, it is possible to identify a suitable region in the protein molecule whose structure can be changed without impairing the biological activity of the protein of the present invention. It is also possible to identify residues or regions in the molecule, which are conserved between similar proteins. Moreover, it is also possible to introduce conservative amino acid substitutions into a region which appears to be important for the biological activity or structure of the protein of the present invention, without impairing the biological activity and without adversely affecting the polypeptide structure of the protein. Particularly in the present invention, the amino acid sequence of the LPAAT of the present invention contains a consensus motif, "HXXXXD ($HX_4D$)," at residues 208-213. This motif is essential for glycerolipid acyltransferase (J. Bacteriology, 180, 1425-1430, 1998) and is also important for the LPAAT of the present invention. Thus, mutants according to the present invention are not limited in any way as long as the above consensus motif is conserved and the above activity of the present invention is not impaired. In the above consensus motif, X represents any amino acid residue.

Those skilled in the art would be able to conduct a so-called structure-function study which identifies residues, in the protein of the present invention and in a similar peptide thereof, that are important for biological activity or structure, and compares amino acid residues between these two peptides, thereby predicting which residues in the protein similar to the protein of the present invention are amino acid residues corresponding to those important for biological activity or structure. Moreover, chemically similar amino acid substitutions may be chosen for the amino acid residues thus predicted to thereby select a mutant which retains the biological activity of the protein of the present invention. Likewise, those skilled in the art would also be able to analyze the three-dimensional structure and amino acid sequence of this protein mutant. The analysis results thus obtained can further be used to predict the alignment of amino acid residues with respect to the three-dimensional structure of the protein. Since amino acid residues predicted to be on the protein surface may be involved in important interactions with other molecules, those skilled in the art would be able to prepare a mutant which causes no change in these amino acid residues predicted to be on the protein surface, on the basis of analysis results as mentioned above. Moreover, those skilled in the art would also be able to prepare a mutant having a single amino acid substitution for any of the amino acid residues constituting the protein of the present invention. These mutants may be screened by any known assay to collect information about the individual mutants, which in turn allows evaluation of the usefulness of individual amino acid residues constituting the protein of the present invention when a comparison is made with the following case where a mutant having substitution of a specific amino acid residue shows lower biological activity than that of the protein of the present invention, where such a mutant shows no biological activity, or where such a mutant produces unsuitable activity to inhibit the biological activity of the protein of the present invention. Moreover, based on information collected from such routine experiments, those skilled in the art may readily analyze amino acid substitutions undesirable for mutants of the protein of the present invention either alone or in combination with other mutations.

As described above, a protein consisting of an amino acid sequence with deletion, substitution or addition of one or more amino acids in the amino acid sequence shown in SEQ ID NO: 2 can be prepared according to techniques such as site-directed mutagenesis as described in "Molecular Cloning, A Laboratory Manual 3rd ed." (Cold Spring Harbor Press (2001)), "Current Protocols in Molecular Biology" (John Wiley & Sons (1987-1997), Kunkel (1985) Proc. Natl. Acad. Sci. USA 82: 488-92, and Kunkel (1988) Method. Enzymol. 85: 2763-6. Preparation of a mutant with such a mutation including amino acid deletion, substitution or addition may be accomplished, for example, by known procedures such as Kunkel method or Gapped duplex method using a mutation-introducing kit based on site-directed mutagenesis such as a QuikChange™ Site-Directed Mutagenesis Kit (Stratagene), a GeneTailor™ Site-Directed Mutagenesis System (Invitrogen) or a TaKaRa Site-Directed Mutagenesis System (e.g., Mutan-K, Mutan-Super Express Km; Takara Bio Inc., Japan).

Techniques for allowing deletion, substitution or addition of one or more amino acids in the amino acid sequences of proteins while retaining their activity include site-directed mutagenesis mentioned above, as well as other techniques such as those for treating a gene with a mutagen, and those in which a gene is selectively cleaved to remove, substitute or add a selected nucleotide or nucleotides, and then ligated.

The present invention is more preferably directed to a protein consisting of an amino acid sequence with deletion, substitution or addition of 1 to 10 amino acids in SEQ ID NO: 2 and having the above activity of the present invention.

There is no limitation on the number or sites of amino acid mutations or modifications in the protein of the present invention, as long as the resulting mutant retains LPAAT activity or the ability to yield the fatty acid rate of LPAAT in the present invention.

LPAAT activity in the present invention or the ability to yield the fatty acid rate of LPAAT in the present invention can be measured in a known manner. For example, reference may be made to the following document: J.B.C., 265, 17215-17221, 1990.

"LPAAT activity" in the present invention may be measured as follows, by way of example. A microsomal fraction is prepared from yeast cells transformed to express the LPAAT of the present invention, as described in, e.g., J. Bacteriology, 173, 2026-2034 (1991). To a reaction solution containing 0.44 mM LPA, 0.36 mM acyl-CoA, 0.5 mM DTT, 1 mg/ml BSA and 2 mM $MgCl_2$ in 50 mM Tris-HCl (pH 7.5), the above microsomal fraction is then added and reacted at 28° C. for an appropriate period. Chloroform:methanol is added to stop the reaction, followed by lipid extraction. The resulting lipids are fractionated by thin-layer chromatography or other techniques, whereby the amount of PA generated can be quantified.

Likewise, "the ability to yield the fatty acid rate of LPAAT" in the present invention may be measured as follows, by way of example. To lyophilized cells obtained by the method of the present invention for preparing a fatty acid composition, chloroform:methanol adjusted to an appropriate ratio is added and stirred, followed by heat treatment for an appropriate period. Centrifugation is further performed to separate the cells and collect the solvent. This procedure is repeated several times. Then, lipids are dried up in an appropriate manner, and a solvent such as chloroform is added to dissolve the lipids. An appropriate aliquot of this sample is treated by the hydrochloric acid/methanol method to derive fatty acids in the cells into corresponding methyl esters, followed by extraction with hexane. After distilling off hexane, the fatty acids are analyzed by gas chromatography.

(b) A nucleotide sequence which is hybridizable under high stringent conditions with a nucleic acid consisting of a nucleotide sequence complementary to a nucleotide sequence consisting of SEQ ID NO: 1 and which encodes a protein having the above activity of the present invention.

Nucleotide sequences contained in the nucleic acids of the present invention include a nucleotide sequence which is hybridizable under high stringent conditions with a nucleic acid consisting of a nucleotide sequence complementary to a nucleotide sequence consisting of SEQ ID NO: 1 and which encodes a protein having the above activity of the present invention, as explained in the section "Homologs of lysophosphatidic acid acyltransferase (LPAAT) 1." SEQ ID NO: 1 and the above activity of the present invention are as described above.

To obtain the above nucleotide sequence, a probe may be prepared from an appropriate fragment in a manner known to those skilled in the art, and this probe may be used in known hybridization techniques such as colony hybridization, plaque hybridization or Southern blotting to obtain the nucleotide sequence from a cDNA library, a genomic library or the like.

As to detailed procedures for hybridization techniques, reference may be made to "Molecular Cloning, A Laboratory Manual 3rd ed." (Cold Spring Harbor Press (2001); particularly Sections 6-7), "Current Protocols in Molecular Biology" (John Wiley & Sons (1987-1997); particularly Sections 6.3-6.4), "DNA Cloning 1: Core Techniques, A Practical Approach 2nd ed." (Oxford University (1995); particularly Section 2.10 for hybridization conditions).

The strength of hybridization is determined primarily by hybridization conditions, more preferably by hybridization conditions and washing conditions. High stringent conditions (highly stringent conditions) include, for example, hybridization conditions of 0.1×SSC to 2×SSC at 55° C. to 65° C., more preferably 0.1×SSC to 1×SSC at 60° C. to 65° C., and most preferably 0.2×SSC at 63° C. In certain cases such as where a hybridization solution contains about 50% formamide, a temperature which is 5° C. to 15° C. lower than the above temperature is used. Washing conditions may be 0.2×SSC to 2×SSC at 50° C. to 68° C., and more preferably 0.2×SSC at 60° C. to 65° C. During hybridization and washing, 0.05% to 0.2% SDS, preferably about 0.1% SDS may usually be added.

A preferred nucleotide sequence falling within the present invention is a nucleotide sequence which is hybridizable under conditions of 1×SSC at 60° C. with a nucleic acid consisting of a nucleotide sequence complementary to a nucleotide sequence consisting of SEQ ID NO: 1 and which encodes a protein having LPAAT activity.

It is also possible to use a commercially available hybridization kit which uses no radioactive substance as a probe. Specific examples include hybridization with a DIG nucleic acid detection kit (Roche Diagnostics) or with an ECL direct labeling & detection system (Amersham).

(c) A nucleotide sequence which consists of a nucleotide sequence sharing an identity of 90% or more with a nucleotide sequence consisting of SEQ ID NO: 1 and which encodes a protein having the above activity of the present invention.

Nucleotide sequences contained in the nucleic acids of the present invention include a nucleotide sequence which consists of a nucleotide sequence being at least 90% or more of the nucleic acid sequence shown in SEQ ID NO: 1 and which encodes a protein having the above activity of the present invention, as explained in the section "Homologs of lysophosphatidic acid acyltransferase (LPAAT) 1."

The present invention includes nucleic acids comprising a nucleotide sequence which shares an identity of at least 90% or more, preferably 93% or more, more preferably 95% or more (e.g., 95%, even more preferably 96%, more particularly 97%, 98% or 99%) with the nucleic acid sequence shown in SEQ ID NO: 1 and which encodes a protein having the above activity of the present invention.

The percent identity between two nucleic acid sequences can be determined by visual inspection and mathematical calculation, or more preferably by using a computer program to compare sequence information between two nucleic acids. Computer programs for sequence comparison include, for example, the BLASTN program (Altschul et al. (1990) J. Mol. Biol. 215: 403-10) version 2.2.7, available for use via the National Library of Medicine website: www.ncbi.nlm.nih.gov/blast/bl2seq/bls.html, or the WU-BLAST 2.0 algorithm. Standard default parameter settings for WU-BLAST 2.0 are described at the following Internet site: blast.wustl.edu.

(d) A nucleotide sequence which encodes an amino acid sequence sharing an identity of 90% or more with an amino acid sequence consisting of SEQ ID NO: 2 and which encodes a protein having the above activity of the present invention.

Nucleotide sequences contained in the nucleic acids of the present invention include a nucleotide sequence which encodes an amino acid sequence sharing an identity of 90% or more with an amino acid sequence consisting of SEQ ID NO: 2 and which encodes a protein having the above activity of the present invention, as explained in the section "Homologs of lysophosphatidic acid acyltransferase (LPAAT) 1."

More specifically, the present invention includes a nucleotide sequence which encodes an amino acid sequence sharing an identity of at least 90% or more, preferably 93% or more, more preferably 95% or more (e.g., 95%, even more preferably 96%, more particularly 97%, 98% or 99%) with the amino acid sequence shown in SEQ ID NO: 2 and which encodes a protein having the above activity of the present invention.

A preferred nucleotide sequence contained in the nucleic acids of the present invention is a nucleotide sequence which encodes an amino acid sequence sharing an identity of 90% or more with an amino acid sequence consisting of SEQ ID NO: 2 and which encodes a protein having the above activity of the present invention. More preferred is a nucleotide sequence which encodes an amino acid sequence sharing an identity of 95% or more with an amino acid sequence consisting of SEQ ID NO: 2 and which encodes a protein having the above activity of the present invention.

The percent identity between two amino acid sequences may be determined by visual inspection and mathematical calculation. Alternatively, the percent identity may be determined by using a computer program. Examples of such a computer program include BLAST, FASTA (Altschul et al., J. Mol. Biol., 215: 403-410 (1990)) and ClustalW. In particular, various conditions (parameters) for an identity search with the BLAST program are described by Altschul et al. (Nucl. Acids. Res., 25, p. 3389-3402, 1997) and publicly available via the website of the National Center for Biotechnology Information (NCBI) or the DNA Data Bank of Japan (DDBJ) (BLAST Manual, Altschul et al., NCB/NLM/NIH Bethesda, Md. 20894; Altschul et al.). It is also possible to use a program such as genetic information processing software GENETYX Ver.7 (Genetyx Corporation, Japan), DINASIS Pro (Hitachisoft, Japan) or Vector NTI (Infomax) for determination of the percent identity.

Certain alignment schemes for aligning amino acid sequences may also result in matching of a specific short region of the sequences, and it is also possible to detect a region with very high sequence identity in such a small aligned region even when there is no significant relationship between the full-length sequences used. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 544-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported).

(e) A nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having the above activity of the present invention.

Nucleotide sequences contained in the nucleic acids of the present invention include a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having the above activity of the present invention, as explained in the section "Homologs of lysophosphatidic acid acyltransferase (LPAAT) 1."

Such a protein consisting of the amino acid sequence shown in SEQ ID NO: 2 and hybridization conditions are as described above. Nucleotide sequences contained in the nucleic acids of the present invention include a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having the above activity of the present invention.

The nucleic acids of the present invention also include a nucleic acid which comprises a nucleotide sequence with deletion, substitution or addition of one or more nucleotides in a nucleotide sequence consisting of SEQ ID NO: 1 and encoding a protein having the above activity of the present invention. More specifically, it is also possible to use a nucleic acid which comprises a nucleotide sequence selected from:

(i) a nucleotide sequence with deletion of one or more (preferably one or several (e.g., 1-144, 1-96, 1-72, 1-48, 1-30, 1-24, 1-20, 1-15, 1-10, more preferably 1-5)) nucleotides in the nucleotide sequence shown in SEQ ID NO: 1;

(ii) a nucleotide sequence with substitution of other nucleotides for one or more (preferably one or several (e.g., 1-144, 1-96, 1-72, 1-48, 1-30, 1-24, 1-20, 1-15, 1-10, more preferably 1-5)) nucleotides in the nucleotide sequence shown in SEQ ID NO: 1;

(iii) a nucleotide sequence with addition of other one or more (preferably one or several (e.g., 1-144, 1-96, 1-72, 1-48, 1-30, 1-24, 1-20, 1-15, 1-10, more preferably 1-5)) nucleotides in the nucleotide sequence shown in SEQ ID NO: 1; or (iv) a nucleotide sequence with any combination of (i) to (iii) above,
and encoding a protein having the above activity of the present invention.

The present invention is more preferably directed to a nucleic acid consisting of a nucleotide sequence and encoding a protein with deletion, substitution or addition of one to several tens of nucleotides, more preferably 1-10 nucleotides in SEQ ID NO: 1 and having the above activity of the present invention.

Lysophosphatidic Acid Acyltransferase Proteins of the Present Invention

LPAAT1-long of the present invention, which may be either naturally occurring or artificially prepared, includes a protein consisting of the amino acid sequence shown in SEQ ID NO: 2 and proteins functionally equivalent to this protein. Such a protein consisting of the amino acid sequence shown in SEQ ID NO: 2 is as described above. "Proteins functionally equivalent" are intended to mean proteins having "the above activity of the present invention," as explained in the section "Nucleic acids of the present invention encoding lysophosphatidic acid acyltransferase" described above.

In the present invention, proteins functionally equivalent to a protein consisting of the amino acid sequence shown in SEQ ID NO: 2 include proteins shown in (a) to (e) below, each of which has the above activity of the present invention:

(a) a protein consisting of an amino acid sequence with deletion, substitution or addition of one or more amino acids in the amino acid sequence shown in SEQ ID NO: 2 and having lysophosphatidic acid acyltransferase activity;

(b) a protein encoded by a nucleotide sequence which is hybridizable under high stringent conditions with a nucleic acid consisting of a nucleotide sequence complementary to a nucleotide sequence consisting of SEQ ID NO: 1 and which encodes a protein having lysophosphatidic acid acyltransferase activity;

(c) a protein encoded by a nucleotide sequence which consists of a nucleotide sequence sharing an identity of 90% or more with a nucleotide sequence consisting of SEQ ID NO: 1 and which encodes a protein having lysophosphatidic acid acyltransferase activity;

(d) a protein consisting of an amino acid sequence sharing an identity of 90% or more with an amino acid sequence consisting of SEQ ID NO: 2 and having lysophosphatidic acid acyltransferase activity; and (e) a protein encoded by a nucleotide sequence which is hybridizable under high stringent conditions with a nucleic acid consisting of a nucleotide sequence complementary to a nucleotide sequence encoding a protein consisting of the amino acid sequence shown in SEQ ID NO: 2 and which encodes a protein having lysophosphatidic acid acyltransferase activity.

Among the above, the amino acid sequence with deletion, substitution or addition of one or more amino acids in SEQ ID NO: 2 or the amino acid sequence sharing an identity of 90% or more with an amino acid sequence consisting of SEQ ID NO: 2 is as explained in the section "Nucleic acids of the present invention encoding lysophosphatidic acid acyltransferase" described above. The phrase "protein which has the above activity of the present invention" is intended to also include mutants of a protein encoded by a nucleic acid comprising the nucleotide sequence of SEQ ID NO: 1, or mutated proteins with various modifications such as substitution, deletion or addition of one or more amino acids in the amino acid sequence shown in SEQ ID NO: 2, as well as their modified proteins whose amino acid side chains or the like are modified, and their fusion proteins with other proteins, as long as these proteins have LPAAT activity and/or the ability to yield the fatty acid rate of LPAAT in the present invention. It should be noted that such a protein functionally equivalent to a protein consisting of the amino acid sequence shown in SEQ ID NO: 2 is more preferably a protein which consists of an amino acid sequence sharing an identity of 95% or more with an amino acid sequence consisting of SEQ ID NO: 2 and which has the above activity of the present invention.

LPAAT1-long of the present invention may also be artificially prepared by chemical synthesis techniques such as Fmoc method (fluorenylmethyloxycarbonyl method) and tBoc method (t-butyloxycarbonyl method). In addition, peptide synthesizers available from Advanced ChemTech, Perkin Elmer, Pharmacia, Protein Technology Instrument, Synthecell-Vega, PerSeptive, Shimadzu Corporation (Japan) or other manufacturers may be used for chemical synthesis.

Cloning of LPAAT Nucleic Acids

Nucleic acids having a specific sequence of LPAAT1-long of the present invention and mutants thereof can be cloned, for example, by screening from a cDNA library using an appropriate probe. They can also be cloned by PCR amplification with appropriate primers and the subsequent ligation to an appropriate vector. The clones thus obtained may further be subcloned into another vector. An explanation will be given below for the case of using a nucleic acid of LPAAT1-long.

For example, it is possible to use commercially available plasmid vectors including pBlue-Script™ SK(+) (Stratagene), pGEM-T (Promega), pAmp (TM: Gibco-BRL), p-Direct (Clontech) and pCR2.1-TOPO (Invitrogen). In the case of using PCR amplification, primers may be any regions of the nucleotide sequence shown in SEQ ID NO: 1. By way of example, it is possible to use the following primers from SEQ ID NO: 1:

Primer 955-1: GGACGTGTCAAGGAAAAGGA (SEQ ID NO: 6) as an upstream primer; and

Primer 955-2: TCCTTCAGATGAGCCTCCTG (SEQ ID NO: 7) as a downstream primer. Then, PCR is performed on cDNA prepared from *M. alpina* cells with the above primers and thermophilic DNA polymerase or the like. Although this procedure can be readily accomplished by those skilled in the art according to, e.g., "Molecular Cloning, A Laboratory Manual 3rd ed." (Cold Spring Harbor Press (2001)), PCR conditions in the present invention may be set as follows, by way of example:

Denaturation temperature: 90-95° C.
Annealing temperature: 40-60° C.
Elongation temperature: 60-75° C.
Number of cycles: 10 or more cycles.

The resulting PCR products may be purified in a known manner, for example, by using a kit (e.g., GENECLEAN (Funakoshi Co., Ltd., Japan), QIAquick PCR purification Kits (QIAGEN), ExoSAP-IT (GE Healthcare Bio-Sciences)), a DEAE-cellulose filter or a dialysis tube. In the case of using an agarose gel, the PCR products are subjected to agarose gel electrophoresis and nucleotide sequence fragments are excised from the agarose gel, followed by purification with GENECLEAN (Funakoshi Co., Ltd., Japan) or QIAquick Gel extraction Kits (QIAGEN) or by the freeze-squeeze method, etc.

The cloned nucleic acids can be determined for their nucleotide sequences with a nucleotide sequencer.

Vector Construction for LPAAT Expression and Transformant Preparation

A recombinant vector carrying a nucleic acid encoding LPAAT1-long of the present invention or a mutant thereof and a transformant transformed with this recombinant vector can be obtained as follows. An explanation will be given below for the case of using a nucleic acid of LPAAT1-long. Namely, a plasmid carrying a nucleic acid encoding LPAAT1-long of the present invention is digested with restriction enzymes. Examples of restriction enzymes available for use include, but are not limited to, EcoRI, KpnI, BamHI and SalI. This digestion may be followed by blunt ending with T4 polymerase. The digested nucleotide sequence fragment is purified by agarose gel electrophoresis. This nucleotide sequence fragment may be integrated into an expression vector in a known manner to obtain a vector for LPAAT1-long expression. This expression vector is introduced into a host to prepare a transformant, which is then provided for expression of a desired protein.

In this case, the types of expression vector and host are not limited in any way as long as they allow expression of a desired protein. Examples of a host include fungi, bacteria, plants, animals or cells thereof. Fungi include filamentous fungi such as lipid-producing *M. alpina*, and yeast strains such as *Saccharomyces cerevisiae*. Bacteria include *Escheri-* chia coli (*E. coli*) and *Bacillus subtilis*. Likewise, plants include oil plants such as rapeseed, soybean, cotton, safflower and flax.

As lipid-producing strains, those such as found in MYCO-TAXON, Vol. XLIV, NO. 2, pp. 257-265 (1992) can be used. Specific examples include microorganisms belonging to the genus *Mortierella*, as exemplified by microorganisms belonging to the subgenus *Mortierella* such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, as well as microorganisms belonging to the subgenus *Micromucor* such as *Mortierella isabellina* CBS194.28, IFO6336, IFO7824, IFO7873, IFO7874, IFO8286, IFO8308, IFO7884, *Mortierella nana* IFO8190, *Mortierella ramanniana* IFO5426, IFO8186, CBS112.08, CBS212.72, IFO7825, IFO8184, IFO8185, IFO8287, *Mortierella vinacea* CBS236.82. Particularly preferred is *Mortierella alpina*.

When a fungus is used as a host, it is desirable that the nucleic acid of the present invention is self-replicable in the host or has a structure insertable onto the fungal chromosome. At the same time, it is preferable to further comprise a promoter and a terminator. When *M. alpina* is used as a host, examples of an expression vector include pD4, pDuraSC and pDura5. Any promoter may be used as long as it allows expression in the host, and examples include promoters derived from *M. alpina*, such as histonH4.1 gene promoter, GAPDH (glyceraldehyde-3-phosphate dehydrogenase) gene promoter and TEF (translation elongation factor) gene promoter.

Techniques for introducing a recombinant vector into filamentous fungi (e.g., *M. alpina*) include electroporation, spheroplast and particle delivery methods, as well as direct microinjection of DNA into nuclei. In the case of using an auxotrophic host strain, strains growing on a selective medium lacking nutrients required for the host strain may be selected to thereby obtain transformed strains. Alternatively, in a case where a drug resistance marker gene is used for transformation, culture may be carried out with a selective medium containing the drug to thereby obtain cell colonies resistant to the drug.

When yeast is used as a host, examples of an expression vector include pYE22m. Alternatively, commercially available yeast expression vectors such as pYES (Invitrogen) and pESC (STRATAGENE) may also be used. Yeast hosts suitable for the present invention include, but are not limited to, *Saccharomyces cerevisiae* strain EH13-15 (trp1, MATα). Examples of a promoter available for use include those derived from yeast or the like, such as GAPDH promoter, gal1 promoter and gal10 promoter.

Techniques for introducing a recombinant vector into yeast cells include lithium acetate, electroporation and spheroplast methods, as well as dextran-mediated transfection, calcium phosphate precipitation, polybrene-mediated transfection, protoplast fusion, encapsulation of polynucleotide(s) in liposomes, and direct microinjection of DNA into nuclei.

When a bacterium such as *E. coli* is used as a host, examples of an expression vector include pGEX and pUC18 available from Pharmacia. Examples of a promoter available for use include those derived from *E. coli*, phage or the like, such as trp promoter, lac promoter, PL promoter and PR promoter. Techniques for introducing a recombinant vector into bacteria include electroporation and calcium chloride methods.

Fatty Acid Compositions of the Present Invention

The present invention provides a fatty acid composition obtained by culturing a host which is transformed with the above recombinant vector carrying LPAAT1-long or the like. More specifically, the fatty acid composition of the present invention is a fatty acid composition obtained by culturing a host which is transformed with a recombinant vector carrying the nucleic acid of the present invention encoding lysophosphatidic acid acyltransferase (i.e., a nucleic acid comprising the nucleotide sequence of SEQ ID NO: 1 or a nucleotide sequence encoding a protein having the amino acid sequence shown in SEQ ID NO: 2 or a mutant functionally equivalent to the nucleic acid), wherein at least one or more of i) to v) shown below:

i) the oleic acid content;
ii) the ratio of the oleic acid content to the palmitic acid content;
iii) the ratio of the oleic acid content to the stearic acid content;
iv) the ratio of the total content of stearic acid and oleic acid to the total content of palmitic acid and palmitoleic acid; and
v) the n-6 fatty acid content is higher in the fatty acid rate of the fatty acid composition than in a cultured product obtained by culturing a host which is not transformed with the recombinant vector of the present invention. The phrase "host which is not transformed with the recombinant vector of the present invention" as used herein is intended to mean, for example, a host transformed with an empty vector carrying none of the nucleic acids described in the section "Nucleic acids of the present invention encoding lysophosphatidic acid acyltransferase."

Fatty acids falling within the present invention may be free fatty acids or may be triglycerides, phospholipids or the like.

Fatty acids contained in the fatty acid composition of the present invention refer to linear or branched monocarboxylic acids of long-chain carbohydrates, including but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo-γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17)), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetradocosanoic acid) (24:0), nervonic acid (cis-15-tetradocosanoic acid) (24:1) and cerotic acid (hexadocosanoic acid) (26:0). It should be noted that the above substance names are common names defined by the IUPAC Biochemical Nomenclature, and their systematic names are given in parentheses along with numerics denoting the number of carbons and the positions of double bonds.

Whether such a fatty acid composition of the present invention is obtained, i.e., whether LPAAT1-long of the present invention is expressed may be confirmed in a manner generally known, for example, as a change in fatty acid rate when LPAAT1-long is expressed in yeast cells. Namely, to lyophilized cells obtained by the above method of the present invention for preparing a fatty acid composition, chloroform:methanol adjusted to an appropriate ratio is added and stirred, followed by heat treatment for an appropriate period. Centrifugation is further performed to separate the cells and collect the solvent. This procedure is repeated several times. Then, lipids are dried up in an appropriate manner, and a solvent such as chloroform is added to dissolve the lipids. An appropriate aliquot of this sample is treated by the hydrochloric acid/methanol method to derive fatty acids in the cells into corresponding methyl esters, followed by extraction with hexane. After distilling off hexane, the fatty acids are analyzed by gas chromatography.

As a result, if a fatty acid composition having the above fatty acid rate is obtained, it can be determined that the fatty acid composition of the present invention was obtained. It should be noted that LPAAT1-long of the present invention yields a fatty acid rate different from that of known LPAAT1 fatty acid compositions, as described above. Namely, upon fatty acid analysis on LPAAT1-long of the present invention and LPAAT1-short used as a model of known LPAAT1, LPAAT1-long of the present invention results in an oleic acid content of around 54%, which is higher than that of LPAAT1-short (around 42%), and it also results in a 1.8- to 2.5-fold higher ratio of the oleic acid content to the palmitic acid content and a 1.8- to 2.3-fold higher ratio of the total content of stearic acid and oleic acid to the palmitic acid content, in comparison with LPAAT1-short. Similarly, the content of n-6 fatty acids is higher in LPAAT1-long than in LPAAT1-short, more specifically the contents of linolic acid, γ-linolenic acid and arachidonic acid are higher in LPAAT1-long than in LPAAT1-short.

This indicates that LPAAT1-long of the present invention has substrate specificity different from that of known LPAATs.

It should be noted that the present invention also provides a fatty acid composition obtained by culturing a host which is transformed with a recombinant vector carrying a nucleic acid comprising the nucleotide sequence of SEQ ID NO: 1 or a nucleotide sequence encoding a protein having the amino acid sequence shown in SEQ ID NO: 2 or a mutant functionally equivalent to the nucleic acid, as described above in the section "Nucleic acids of the present invention encoding lysophosphatidic acid acyltransferase," wherein the ratio of long-chain fatty acids and/or the content of n-6 fatty acids is higher in the fatty acid composition than in a cultured product obtained by culturing a host which is not transformed with the recombinant vector. The term "long-chain" means that a carbon chain constituting a fatty acid has a longer length. For example, stearic acid or oleic acid containing 18 carbon atoms has a longer chain than palmitic acid or palmitoleic acid containing 16 carbon atoms. N-6 fatty acids are as explained in the section "Nucleic acids of the present invention encoding lysophosphatidic acid acyltransferase" described above. The fatty acid composition of the present invention can be regarded as a fatty acid composition having a higher content of oleic acid and a higher ratio of the oleic acid content to the palmitic acid content, as well as having a higher ratio of long-chain fatty acids or a higher content of n-6 fatty acids, in comparison with a cultured product obtained by culturing a host which is not transformed with a recombinant vector carrying a nucleic acid encoding LPAAT1-long. Moreover, depending on the type of host selected in the method of the present invention for preparing a fatty acid composition, it is also possible to prepare a fatty acid composition having a high ratio of longer-chain fatty acids or a high content of n-6 fatty acids. Examples of such a host include fungi, plants, animals or cells thereof. Fungi include filamentous fungi such as lipid-producing *M. alpina*, and yeast strains such as *Saccharomyces cerevisiae*. Likewise, plants include oil plants such as rapeseed, soybean, cotton, safflower and flax. In this case, long-chain fatty acids whose content is higher than that of fatty acids in a cultured product obtained by culturing a host which is not transformed with a recombinant vector carrying the nucleic acid of the present invention include, but are not limited to, oleic acid, linolic acid, γ-linolenic acid, DGLA, α-linolenic acid, stearidonic acid, arachidonic acid, eicosapentaenoic acid, docosapentaenoic acid, and docosahexaenoic acid. N-6 fatty acids include, but are not limited to, linolic acid, γ-linolenic acid, DGLA and arachidonic acid. Fatty acid compositions having a high ratio of such longer-chain fatty acids are preferred because they can be advantageous for use in nutritional supplementary foods, health foods, functional foods, children's foods, infant modified milk, premature infant modified milk, geriatric foods, etc.

Method of the Present Invention for Preparing a Fatty Acid Composition

The present invention also provides a method for preparing these fatty acid compositions. The method of the present invention is characterized by using LPAAT1-long described above. More specifically, the present invention relates to a method for preparing a fatty acid composition, which comprises collecting a fatty acid composition from a cultured product obtained by culturing a host which is transformed with a recombinant vector carrying a nucleic acid comprising the nucleotide sequence of SEQ ID NO: 1 or a nucleotide sequence encoding a protein having the amino acid sequence shown in SEQ ID NO: 2 or a mutant functionally equivalent to the nucleic acid, wherein the fatty acid composition has a higher value for at least one or more of i) to v) shown below:

i) the oleic acid content;
ii) the ratio of the oleic acid content to the palmitic acid content;
iii) the ratio of the oleic acid content to the stearic acid content;
iv) the ratio of the total content of stearic acid and oleic acid to the total content of palmitic acid and palmitoleic acid; and
v) the n-6 fatty acid content in comparison with a cultured product obtained by culturing a host which is not transformed with the recombinant vector.

For culture of organisms transformed to express LPAAT1-long, any medium may be used as long as it is a culture solution (medium) having appropriate pH and osmotic pressure as well as containing nutrients required for growth of each host, trace elements, and biomaterials such as serum or antibiotics. For example, in the case of yeast cells transformed to express LPAAT1-long, SC-Trp medium, YPD medium, YPD5 medium or the like may be used without being limited thereto. Detailed medium composition is illustrated for SC-Trp medium: 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil) per liter of medium.

Any culture conditions may be used as long as they are suitable for host growth and are adequate for maintenance of the generated enzyme in a stable state. More specifically, individual conditions may be adjusted, including anaerobic degree, culture period, temperature, humidity, static culture or shaking culture. Culture may be accomplished under the same conditions (one-step culture) or by so-called two-step or three-step culture using two or more different culture conditions. For large-scale culture, two-step or more step culture is preferred because of its high culture efficiency.

To explain detailed procedures for the method of the present invention for preparing a fatty acid composition, two-step culture in a yeast host will be illustrated below as an example. Namely, in the pre-culture step, the colonies obtained above are inoculated into any medium described above (e.g., SC-Trp medium) and cultured with shaking at 30° C. for 2 days. Then, in the main culture step, the pre-cultured solution (500 µl) is added to 10 ml YPD5 (2% yeast extract, 1% polypeptone, 5% glucose) medium and cultured with shaking at 30° C. for 2 days.

Use of Nucleic Acids of the Present Invention

The present invention further provides the use of LPAAT1-long described above for the manufacture of the fatty acid composition of the present invention.

More specifically, the present invention provides the use of the LPAAT-encoding nucleic acid of the present invention for the manufacture of the fatty acid composition of the present invention.

Using the above nucleic acid is preferred because it enables not only the preparation of the fatty acid composition of the present invention, but also the preparation of food or other products comprising the fatty acid composition, which achieve the intended purposes, as explained in the section "Food or other products comprising fatty acid compositions of the present invention" described below.

Food or Other Products Comprising Fatty Acid Compositions of the Present Invention The present invention further provides a food product comprising the above fatty acid composition. The fatty acid composition of the present invention can be used in a routine manner for purposes such as production of food products containing fats and oils as well as production of industrial source materials (those for cosmetics, pharmaceuticals (e.g., external preparations for skin), soaps, etc.). Cosmetics (cosmetic compositions) or pharmaceuticals (pharmaceutical compositions) may be formulated into any dosage form including, but not limited to, solutions, pastes, gels, solids or powders. Likewise, possible forms of food products include pharmaceutical formulations such as capsules, as well as processed foods such as ordinary fluid diets, semi-digested nourishing diets, elemental diets, drinkable preparations or enteral nutrient preparations, which comprise the fatty acid composition of the present invention in admixture with proteins, sugars, fats, trace elements, vitamins, emulsifiers, flavorings, etc.

Moreover, examples of the food product of the present invention include, but are not limited to, nutritional supplementary foods, health foods, functional foods, children's foods, infant modified milk, premature infant modified milk, and geriatric foods. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use.

The term "children's foods" refers to food products given to children up to about 6 years old. The term "geriatric foods" refers to food products treated to facilitate digestion and absorption when compared to untreated foods. The term "infant modified milk" refers to modified milk given to children up to about one year old. The term "premature infant modified milk" refers to modified milk given to premature infants until about 6 months after birth.

These food products include natural foods (treated with fats and oils) such as meat, fish and nuts; foods supplemented with fats and oils during preparation (e.g., Chinese foods, Chinese noodles, soups); foods prepared using fats and oils as heating media (e.g., tempura (deep-fried fish and vegetables), deep-fried foods, fried bean curd, Chinese fried rice, doughnuts, Japanese fried dough cookies (karinto)); fat- and oil-based foods or processed foods supplemented with fats and oils during processing (e.g., butter, margarine, mayonnaise, dressing, chocolate, instant noodles, caramel, biscuits, cookies, cake, ice cream); and foods sprayed or coated with fats and oils upon finishing (e.g., rice crackers, hard biscuits, sweet bean paste bread). However, the food product of the present invention is not limited to foods containing fats and oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine (sake), medicinal liquor, sweet cooking sherry (mirin), vinegar, soy sauce and miso (bean paste); livestock food products such as yogurt, ham, bacon and sausage; seafood products such as fish cake (kamaboko), deep-fried fish cake (ageten) and puffy fish cake (hanpen); as well as fruit drinks, soft drinks, sports drinks, alcoholic beverages, and tea.

Method for Strain Evaluation or Selection Using Nucleic Acids or Proteins Related to the Present Invention The present invention also provides a method for evaluating or selecting a lipid-producing strain using the nucleic acids or proteins related to the present invention. Details are given below.

(1) Evaluation Method

One embodiment of the present invention is a method for evaluating a lipid-producing strain using the LPAAT1-long-encoding nucleic acid or LPAAT1-long protein of the present invention. As a first example for the above evaluation method of the present invention, lipid-producing test strains are evaluated for the above activity of the present invention by using primers or probes designed based on the nucleotide sequence of the present invention. General procedures for such evaluation are known and can be found in, e.g., International Patent Publication No. WO01/040514 or JP 8-205900 A. A brief explanation will be given below of this evaluation.

First, the genome of a test strain is prepared. For genome preparation, it is possible to use any known technique such as Hereford method or potassium acetate method (see, e.g., Methods in Yeast Genetics, Cold Spring Harbor Laboratory Press, p 130 (1990)).

Primers or probes are designed based on the nucleotide sequence of the present invention, preferably SEQ ID NO: 1. These primers or probes may be any regions of the nucleotide sequence of the present invention, and known procedures may be used for their design. The number of nucleotides in a polynucleotide used as a primer is generally 10 nucleotides or more, preferably 15 to 25 nucleotides. Likewise, the number of nucleotides appropriate for a region to be flanked by primers is generally 300 to 2000 nucleotides.

The primers or probes prepared above are used to examine whether the genome of the above test strain contains a sequence specific to the nucleotide sequence of the present invention. A sequence specific to the nucleotide sequence of the present invention may be detected using known procedures. For example, a polynucleotide comprising a part or all of a sequence specific to the nucleotide sequence of the present invention or a polynucleotide comprising a nucleotide sequence complementary to the above nucleotide sequence is used as one primer, and a polynucleotide comprising a part or all of a sequence located upstream or downstream of this sequence or a polynucleotide comprising a nucleotide sequence complementary to the above nucleotide sequence is used as the other primer to amplify nucleic acids from the test strain by PCR or other techniques, followed by determining the presence or absence of amplification products, the molecular weight of amplification products, etc.

PCR conditions suitable for the method of the present invention are not limited in any way, and may be set as follows, by way of example:

Denaturation temperature: 90-95° C.
Annealing temperature: 40-60° C.
Elongation temperature: 60-75° C.
Number of cycles: 10 or more cycles.

The resulting reaction products may be separated by electrophoresis on an agarose gel or the like to determine the molecular weight of the amplification products. Each amplification product is then confirmed as to whether its molecular weight is a size enough to cover a nucleic acid molecule corresponding to a region specific to the nucleotide sequence of the present invention, whereby the test strain can be predicted or evaluated for the above activity of the present invention. Moreover, if the above amplification products are analyzed for their nucleotide sequences, as described above, the above activity of the present invention can be predicted or evaluated with more accuracy. It should be noted that procedures for evaluating the above activity of the present invention are as described above.

As another example for the above evaluation method of the present invention, a test strain is cultured and measured for the expression level of LPAAT1-long encoded by the nucleotide sequence of the present invention (e.g., SEQ ID NO: 1), whereby the test strain can be evaluated for the above activity of the present invention. It should be noted that the expression level of LPAAT1-long can be measured by culturing a test strain under appropriate conditions and quantifying mRNA or protein for LPAAT1-long. Quantification of mRNA or protein may be accomplished by using known procedures, for example, Northern hybridization or quantitative RT-PCR for mRNA quantification and Western blotting for protein quantification (Current Protocols in Molecular Biology, John Wiley & Sons 1994-2003). For evaluation of the above activity, it is also possible to measure the fatty acid rate of a fatty acid composition produced by LPAAT1-long of the present invention. Procedures for measuring the fatty acid rate of a fatty acid composition are as described above.

(2) Selection Method

Another embodiment of the present invention is a method for selecting a lipid-producing strain using the LPAAT1-long-encoding nucleic acid or LPAAT1-long protein of the present invention. As an example for the above selection method of the present invention, test strains are cultured and measured for the expression level of LPAAT1-long encoded by the nucleotide sequence of the present invention (e.g., SEQ ID NO: 1) to select a strain with a desired expression level, whereby a strain having a desired activity can be selected. Alternatively, a type strain is predetermined, and this type strain and test strains are each cultured and measured for the above expression level, followed by comparison of the expression level between the type strain and each test strain, whereby a desired strain can be selected. More specifically, for example, a type strain and test strains are cultured under appropriate conditions and measured for their expression levels to select a test strain showing higher or lower expression than the type strain, whereby a strain having a desired activity can be selected. Examples of a desired activity include the expression level of LPAAT1-long and the fatty acid rate of a fatty acid composition produced by LPAAT1-long, which may be measured as described above.

As another example for the above selection method of the present invention, test strains are cultured to select a strain in which the above activity of the present invention is high or low, whereby a strain having a desired activity can be selected. Examples of a desired activity include the expression level of LPAAT1-long and the fatty acid rate of a fatty acid composition produced by LPAAT1-long, which may be measured as described above.

Examples of a test strain or type strain available for use include, but are not limited to, a strain transformed with the above vector of the present invention, a strain modified to suppress expression of the above nucleic acid of the present invention, a strain modified by mutagenesis, and a strain having natural mutation(s). It should be noted that LPAAT1-long activity in the present invention and the ability to yield the fatty acid rate of LPAAT1-long in the present invention can be measured, for example, by the procedures described in the sections "Nucleic acids of the present invention encoding lysophosphatidic acid acyltransferase" and "Fatty acid compositions of the present invention." Mutagenesis may be accomplished by, but not limited to, physical techniques including ultraviolet or radioactive irradiation, or chemical techniques including treatment with an agent such as EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Strains used in the present invention as type and test strains include, but are not limited to, the above lipid-producing strains or yeast strains. More specifically, the type strain or test strain may be a combination of any strains belonging to different genera or species, and one or more test strains may be used simultaneously.

The present invention will now be described in more detail by way of the following examples, which are not intended to limit the scope of the invention.

EXAMPLE 1

(1) EST Analysis

*M. alpina* strain 1S-4 was inoculated into 100 ml medium (1.8% glucose, 1% yeast extract, pH 6.0) and pre-cultured for 3 days at 28° C. A 10 L culture vessel (Able Co., Tokyo) was charged with 5 L medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using an Oligotex-dT30<Super>mRNA Purification Kit (Takara Bio Inc., Japan) ('dT30' disclosed as SEQ ID NO: 29), poly(A)$^+$RNA was purified from the total RNA. A cDNA library was prepared for each stage with a ZAP-cDNA GigapackIII Gold Cloning Kit (STRATAGENE), followed by one-pass sequence analysis from the 5'-end of cDNA (8000 clones×5 stages). The resulting sequences were clustered. As a result, about 5000 sequences were obtained.

(2) Search for LPAAT Gene Homologs

The nucleotide sequences obtained from EST analysis were searched against amino acid sequences registered in GENEBANK with a homology search program, BLASTX, to extract homologs of the LPAAT gene. As a result, an LPAAT homolog sequence (SEQ ID NO: 5) was found. SEQ ID NO: 5 was found to share the highest identity with a *Neurospora crassa*-derived 1-acyl-sn-glycerol-3-phosphate acyltransferase-like putative protein (GB accession No. EAA28956).

The *M. alpina* LPAAT homolog (LPAAT1) sequence shown in the specification of Patent Document 2 was compared with the sequence obtained above, indicating that SEQ ID NO: 5 was a partial sequence of an isoallele of LPAAT1.

With respect to the above sequence, its source libraries and ESTs are as shown in Table 2. It should be noted that in Table 2, clones are classified by the day of culture on which their source cDNA libraries were obtained.

TABLE 2

| | Source library | | | | |
|---|---|---|---|---|---|
| Days of culture | 1 | 2 | 3 | 6 | 8 |
| Number of clones | | 1 | | 1 | 3 |

EXAMPLE 2

(1) Cloning of LPAAT Homologs

SEQ ID NO: 5 contains no CDS appearing to encode a LPAAT homolog. Thus, for cloning of cDNA encoding the full length of this gene, primers were prepared based on this sequence as follows.
Primers Designed Based on SEQ ID NO: 5:

```
Primer 955-1:
GGACGTGTCAAGGAAAAGGA      (SEQ ID NO: 6)

Primer 955-2:
TCCTTCAGATGAGCCTCCTG      (SEQ ID NO: 7)
```

Using these primers, PCR was performed with ExTaq (Takara Bio Inc., Japan) by using a cDNA library containing ESTs constituting SEQ ID NO: 5 as a template. The resulting DNA fragments were TA-cloned with a TOPO-TA cloning Kit (INVITROGEN CORPORATION) to determine the nucleotide sequence of an insert.

The results confirmed that a DNA fragment covering nucleotides 20-518 of SEQ ID NO: 5 was cloned. This plasmid was designated as pCR-955-P. Then, this plasmid was used as a template to perform PCR with the above primers. In PCR, ExTaq (Takara Bio Inc., Japan) was used, but the attached dNTP mix was replaced by a PCR labeling mix (Roche Diagnostics) for digoxigenin (DIG) labeling of DNA to be amplified, thereby preparing a probe for use in cDNA library screening. This probe was used to screen the cDNA library from which the ESTs constituting the above sequence had been obtained by EST analysis.

Hybridization conditions were set as follows.
Buffer: 5×SSC, 1% SDS, 50 mM Tris-HCl (pH 7.5), 50% formamide
Temperature: 42° C. (overnight)
Washing conditions: in 0.2×SSC, 0.1% SDS at 65° C. for 20 minutes (repeated three times)

Detection was accomplished by using a DIG nucleic acid detection kit (Roche Diagnostics). From phage clones obtained by screening, the plasmid was excised by in vivo excision to obtain plasmid DNA.

The nucleotide sequence of an insert from a clone with the longest insert obtained by screening of cDNA containing SEQ ID NO: 5 is shown in SEQ ID NO: 3. SEQ ID NO: 3 contains a coding region of 1443 bp between positions 116 and 1557, thus suggesting that a sequence encoding the full length of LPAAT homolog was obtained. The deduced amino acid sequence of a protein encoded by this gene is shown in SEQ ID NO: 2.

During the screening of cDNA containing SEQ ID NO: 5, another clone was also obtained, which was an insert shorter than SEQ ID NO: 3. The nucleotide sequence of an insert from the resulting clone is shown in SEQ ID NO: 9. SEQ ID NO: 9 contains an ORF of 1251 bp between positions 36 and 1286, thus indicating that this sequence was identical to 5'-terminal nucleotides 193-1443 of the nucleotide sequence shown in SEQ ID NO: 1. Namely, the nucleotide sequence shown in SEQ ID NO: 9 was shorter than the nucleotide sequence shown in SEQ ID NO: 1 by 192 nucleotides in the 5'-region. The deduced amino acid sequence of a protein encoded by this gene is shown in SEQ ID NO: 10.

The plasmid containing SEQ ID NO: 3 was designated as pB-LPAAT1-long, while the plasmid containing SEQ ID NO: 9 was designated as pB-LPAAT1-short. Likewise, the gene of SEQ ID NO: 3 was referred to as the LPAAT1-long gene, while the gene of SEQ ID NO: 9 was referred to as the LPAAT1-short gene.

(2) Sequence Analysis

The thus obtained cDNA sequences of *M. alpina*-derived LPAAT homologs were subjected to BLASTX homology analysis against amino acid sequences registered in GENEBANK. As a result, amino acid sequences having the lowest E-value, i.e., sharing the highest identity with each sequence are as shown below. The sequences sharing the highest identity were analyzed by clustalW to determine their identity with ORF of each sequence at the nucleotide and amino acid sequence levels, which are also shown below.

SEQ ID NO: 3 was found to have an identity of 51% at the nucleotide sequence level and 32.1% at the amino acid sequence level, in comparison with a corresponding region of an *Aspergillus nidulans*-derived 1-acyl-sn-glycerol-3-phosphate acyltransferase-like putative protein (GB accession No. EAA60126).

SEQ ID NO: 9 was found to have an identity of 51% at the nucleotide sequence level and 32.1% at the amino acid sequence level, in comparison with a corresponding region of an *Aspergillus nidulans*-derived 1-acyl-sn-glycerol-3-phosphate acyltransferase-like putative protein (GB accession No. EAA60126).

SEQ ID NOs: 3 and 9 were also each compared with a *M. alpina*-derived known LPAAT homolog, i.e., LPAAT1 gene (Patent Document 2) and with deduced amino acid sequence encoded by this gene. The sequence disclosed in the above document and the sequences obtained from *M. alpina* strain 1S-4 were compared with each other in their corresponding regions, confirming that LPAAT1-long and LPAAT1-short both had an identity of 89% at the nucleotide sequence level and 91% at the amino acid sequence level.

EXAMPLE 3

Construction of Yeast Expression Vector

To express LPAAT1-long and LPAAT1-short in yeast cells, yeast expression vectors were constructed as follows.

The plasmid pB-LPAAT1-long was digested with restriction enzymes EcoRI and KpnI to obtain a DNA fragment of approximately 1.7 kb, which was then inserted into the EcoRI-KpnI site of yeast expression vector pYE22m (Biosci. Biotech. Biochem., 59, 1221-1228, 1995) to construct plasmid pYE-MALPAA1-long.

To express LPAAT1-short in yeast cells, a yeast expression vector was constructed as follows. Namely, the plasmid pB-LPAAT1-short was used as a template to perform PCR with the following primers LPAAT1-6F (SEQ ID NO: 11) and LPAAT1-R1 (SEQ ID NO: 12) using ExTaq (Takara Bio Inc., Japan).

```
LPAAT1-6F:
TCTGAGATGGATGAATCCACCACCACCAC          (SEQ ID NO: 11)

LPAAT1-R1:
GTCGACTCAACCAGACGATACTTGCTGCAGAG       (SEQ ID NO: 12)
```

The resulting DNA fragments were TA-cloned with a TOPO-TA cloning Kit (INVITROGEN) to confirm the nucleotide sequence of each insert. A plasmid carrying the correct nucleotide sequence was designated as pCR-LPAAT1-short. This plasmid was digested with restriction enzymes EcoRI and SalI to obtain a DNA fragment of approximately 1.3 kb, which was then inserted into the EcoRI-SalI site of yeast expression vector pYE22m to construct plasmid pYE-MALPAAT1-short.

EXAMPLE 4

Yeast Transformation

The plasmid pYE22m, pYE-MALPAA1-long or pYE-MALPAAT1-short was used to transform yeast *Saccharomyces cerevisiae* strain EH13-15 (trp1, MATα) (Appl. Microbiol. Biotechnol., 30, 515-520, 1989) by the lithium acetate method. The transformed strains were screened by the ability to grow on SC-Trp agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

EXAMPLE 5

Yeast Culture

Among the transformed strains obtained with each vector, any two strains (strains c-1 and c-2, strains LPAAT1-long-1 and LPAAT1-long-2, or strains LPAAT1-short-1 and LPAAT1-short-2) were selected and cultured under the following conditions.

Namely, in the pre-culture step, a loopful of each yeast strain was inoculated from the plate into SC-Trp medium (10 ml) and cultured with shaking at 30° C. for 2 days. In the main culture step, the pre-cultured solution (500 µl) was added to 10 ml YPD5 (2% yeast extract, 1% polypeptone, 5% glucose) medium and cultured with shaking at 30° C. for 2 days.

EXAMPLE 6

Fatty Acid Analysis of Yeast Strains

The cultured yeast solutions were each centrifuged to collect the cells. After washing with 10 ml sterilized water, the cells were collected again by centrifugation and lyophilized. To the lyophilized cells, chloroform:methanol (2:1, 4 ml) was added and stirred vigorously, followed by incubation at 70° C. for 1 hour. The cells were separated by centrifugation to collect the solvent. To the remaining cells, chloroform:methanol (2:1, 4 ml) was added again, and the same procedure was repeated to collect the solvent. After lipids were dried up with a SpeedVac, 2 ml chloroform was added to dissolve the lipids. A 200 µl aliquot of this sample was treated by the hydrochloric acid/methanol method to derive fatty acids in the cells into corresponding methyl esters, followed by extraction with hexane. After distilling off hexane, the fatty acids were analyzed by gas chromatography.

The results obtained are shown in Table 3.

TABLE 3

Fatty acid rate of transformed strains (host: EH13-15)

| Sample name | 1 pYE22m-1 | 2 pYE22m-2 | 3 LPAAT1 (short)-1 | 4 LPAAT1 (short)-2 | 5 (present invention) LPAAT1 (long)-1 | 6 (present invention) LPAAT1 (long)-2 |
|---|---|---|---|---|---|---|
| 16:0 (palmitic acid) | 8.60 | 6.58 | 12.17 | 14.76 | 7.66 | 7.49 |
| 16:1 (palmitoleic acid) | 39.52 | 42.40 | 34.69 | 34.44 | 33.00 | 32.54 |
| 18:0 (stearic acid) | 5.28 | 4.62 | 4.73 | 5.10 | 3.73 | 3.69 |
| 18:1 (oleic acid) | 44.07 | 43.74 | 45.88 | 42.40 | 54.04 | 53.91 |
| Other fatty acids | 2.53 | 2.66 | 2.53 | 3.31 | 1.58 | 2.37 |
| Total | 100.00 | 100.00 | 100.00 | 100.00 | 100.00 | 100.00 |
| 16:1/16:0 | 4.59 | 6.45 | 2.85 | 2.33 | 4.31 | 4.34 |
| 18:1/18:0 | 8.35 | 9.48 | 9.71 | 8.32 | 14.49 | 14.62 |
| 18:1 + 16:1/18:0 + 16:0 | 6.02 | 7.70 | 4.77 | 3.87 | 7.64 | 7.73 |
| 18:0/16:0 | 0.61 | 0.70 | 0.39 | 0.35 | 0.49 | 0.49 |
| 18:1/16:1 | 1.12 | 1.03 | 1.32 | 1.23 | 1.64 | 1.66 |
| 18:0 + 18:1/16:0 + 16:1 | 1.03 | 0.99 | 1.08 | 0.97 | 1.42 | 1.44 |
| 18:1/16:0 | 5.12 | 6.65 | 3.77 | 2.87 | 7.06 | 7.19 |

The yeast strains transformed with two LPAAT homologs derived from *M. alpina* and the control yeast strains were compared for their fatty acid rate. In the fatty acid rate of the LPAAT1-short-transformed yeast, the percentage of palmitic acid increased, but the palmitoleic acid content decreased when compared to the control strains. Thus, the ratio of the palmitoleic acid content to the palmitic acid content was lower than that of the control strains. The stearic acid and oleic acid contents were the same as in the control strains.

In contrast, in the LPAAT1-long-transformed yeast, the percentage of oleic acid increased by 10% or more when compared to the control strains, whereas the percentages of palmitoleic acid and stearic acid both decreased. Thus, the ratio of the oleic acid content to the palmitic acid content and the ratio of the oleic acid content to the stearic acid content were higher than those of the control strains. The ratio of the total content of stearic acid and oleic acid to the total content of palmitic acid and palmitoleic acid was also higher than that of the control strains.

These results indicated that two LPAAT homologs derived from *M. alpina* had different specificity for their substrate acyl group, and hence yeast strains transformed with these genes yielded completely different fatty acid rates from homolog to homolog. The results also indicated that it was possible to breed organisms with a desired fatty acid rate when the above homologs were selected to suit the intended purpose.

EXAMPLE 7

(1) Breeding of Arachidonic Acid-Producing Yeast Strains

To breed arachidonic acid-producing yeast (*Saccharomyces cerevisiae*) strains, the following plasmids were constructed.

First, cDNA prepared from *M. alpina* strain 1S-4 was used as a template to perform PCR with ExTaq using a primer set of Δ12-f and Δ12-r, Δ6-f and Δ6-r, GLELO-f and GLELO-r, or Δ5-f and Δ5-r to thereby amplify the Δ12 fatty acid desaturase gene, the Δ6 fatty acid desaturase gene, the GLELO fatty acid elongase gene or the 45 fatty acid desaturase gene in the *M. alpina* strain 1S-4.

```
Δ12-f:
TCTAGAATGGCACCTCCCAACACTATTG    (SEQ ID NO: 13)

Δ12-r:
AAGCTTTTACTTCTTGAAAAAGACCACGTC  (SEQ ID NO: 14)

Δ6-f:
TCTAGAATGGCTGCTGCTCCCAGTGTGAG   (SEQ ID NO: 15)

Δ6-r:
AAGCTTTTACTGTGCCTTGCCCATCTTGG   (SEQ ID NO: 16)

GLELO-f:
TCTAGAATGGAGTCGATTGCGCAATTCC    (SEQ ID NO: 17)

GLELO-r:
GAGCTCTTACTGCAACTTCCTTGCCTTCTC  (SEQ ID NO: 18)

Δ5-f:
TCTAGAATGGGTGCGGACACAGGAAAAACC  (SEQ ID NO: 19)

Δ5-r:
AAGCTTTTACTCTTCCTTGGGACGAAGACC  (SEQ ID NO: 20)
```

These genes were cloned with a TOPO-TA-cloning Kit. The clones were confirmed for their nucleotide sequences, and those containing the nucleotide sequences of SEQ ID NOs: 21-24 were designated as plasmids pCR-MAΔ12DS (containing the nucleotide sequence of SEQ ID NO: 21), pCR-MAΔ6DS (containing the nucleotide sequence of SEQ ID NO: 22), pCR-MAGLELO (containing the nucleotide sequence of SEQ ID NO: 23) and pCR-MAΔ5DS (containing the nucleotide sequence of SEQ ID NO: 24), respectively.

Next, the plasmid pCR-MAΔ12DS was digested with a restriction enzyme HindIII and, after blunt ending, was further digested with a restriction enzyme XbaI to obtain a DNA fragment of approximately 1.2 kbp, while vector pESC-URA (STRATAGENE) was digested with a restriction enzyme SacI and, after blunt ending, was further digested with a restriction enzyme SpeI to obtain a DNA fragment of approximately 6.6 kbp. These DNA fragments were ligated to obtain plasmid pESC-U-Δ12. The plasmid pCR-MAΔ6DS was digested with a restriction enzyme XbaI and, after blunt ending, was further digested with a restriction enzyme HindIII to obtain a DNA fragment of approximately 1.6 kbp, while the plasmid pESC-U-Δ12 was digested with a restriction enzyme SalI and, after blunt ending, was further digested with a restriction enzyme HindIII to obtain a DNA fragment of approximately 8 kbp. These DNA fragments were ligated to obtain plasmid pESC-U-Δ12:Δ6. This plasmid was partially digested with a restriction enzyme PvuII, and the resulting fragment of approximately 4.2 kb was inserted into the SmaI site of pUC-URA3 to obtain plasmid pUC-URA-Δ12:Δ6.

Likewise, the plasmid pCR-MAGLELO was digested with restriction enzymes XbaI and SacI to obtain a DNA fragment of approximately 0.95 kbp, while vector pESC-LEU (STRATAGENE) was digested with restriction enzymes XbaI and SacI to obtain a DNA fragment of approximately 7.7 kbp. These DNA fragments were ligated to obtain plasmid pESC-L-GLELO. The plasmid pCR-MAΔ5DS was digested with a restriction enzyme XbaI and, after blunt ending, was further digested with a restriction enzyme HindIII to obtain a DNA fragment of approximately 1.3 kbp, while the plasmid pESC-L-GLELO was digested with a restriction enzyme ApaI and, after blunt ending, was further digested with a restriction enzyme HindIII to obtain a DNA fragment of approximately 8.7 kbp. These DNA fragments were ligated to obtain plasmid pESC-L-GLELO:Δ5. This plasmid was digested with a restriction enzyme PvuII, and the resulting fragment of approximately 3.2 kb was inserted into the SmaI site of pUC-LEU2 to obtain plasmid pUC-LEU-GLELO:Δ5.

*S. cerevisiae* strain YPH499 (STRATAGENE) was co-transformed with plasmid pUC-URA-Δ12:Δ6 and plasmid pUC-LEU-GLELO:Δ5. The transformed strains were screened by the ability to grow on SC-Leu,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine, 6 g threonine and 1.2 g tryptophan). Among the strains thus obtained, any one strain was designated as strain ARA3-1.

(2) Obtaining and Analysis of Transformed Strains of Arachidonic Acid-Producing Yeast The strain ARA3-1 was transformed respectively with plasmids pYE22m, pYE-MALPAAT1-long and pYE-MAL-PAAT1-short. The transformed strains were screened by the ability to grow on SC-Trp,Leu,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine). Among the strains thus transformed, any 4 strains were selected for each plasmid.

These strains were each cultured at 30° C. for 1 day in the above SC-Trp,Leu,Ura liquid medium (10 ml), 1 ml of which was then cultured at 15° C. for 7 days in SG-Trp,Leu,Ura liquid medium (10 ml) containing, per liter, 6.7 g Yeast nitrogen base w/o amino acids (DIFCO), 20 g galactose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine), followed by analysis of fatty acids in the cells. Table 4 shows the fatty acid rate in the cells.

TABLE 4

| Ratio (%) of n-6 PUFA to total fatty acid | | | |
| --- | --- | --- | --- |
| | Control | LPAAT1-long | LPAAT1-short |
| Linolic acid | 8.37 ± 0.26 | 12.61 ± 0.43 | 10.02 ± 2.17 |
| γ-Linolenic acid | 0.54 ± 0.07 | 1.54 ± 0.14 | 0.89 ± 0.46 |
| DGLA | 0.33 ± 0.02 | 0.48 ± 0.03 | 0.50 ± 0.03 |
| Arachidonic acid | 0.44 ± 0.03 | 0.79 ± 0.08 | 0.58 ± 0.14 |

As shown above, high expression of LPAAT1-long in the yeast strain bred to allow arachidonic acid production resulted in a higher ratio of n-6 PUFA to total fatty acid, when compared to the control strains transformed with the vector alone. Moreover, high expression of LPAAT1-long also resulted in higher ratios of linolic acid, γ-linolenic acid and arachidonic acid, when compared to high expression of LPAAT1-short.

EXAMPLE 8

Vector Construction for *M. alpina* Expression

The vector used for *M. alpina* expression was pDuraSC which allows expression of a desired gene from the GAPDH promoter.

To express LPAAT1-long and LPAAT1-short in *M. alpina* cells, vectors were constructed as follows. Namely, the plasmid pB-LPAAT1-long was digested with restriction enzymes EcoRI and SalI. Among the resulting DNA fragments, a fragment of approximately 1.5 kb was excised and inserted into the EcoRI-XhoI sites in the multicloning site of vector pDuraSC to construct plasmid pDuraSC-LPAAT1-long. Likewise, the plasmid pCR-LPAAT1-short was digested with EcoRI and SalI. Among the resulting DNA fragments, a fragment of approximately 1.3 kb was excised and inserted into the EcoRI-XhoI sites in the multicloning site of vector pDuraSC to construct pDura5SC-LPAAT1-short.

EXAMPLE 9

Obtaining of Transformed *M. alpina* Strains

Uracil-auxotrophic strain Aura-3 derived from *M. alpina* as described in a patent document (WO2005/019437 entitled "Method of Breeding Lipid-Producing Fungus") was used as a host and transformed with these plasmids by the particle delivery method. For screening of the transformed strains, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

EXAMPLE 10

Evaluation of *M. alpina* Transformants

The resulting transformed strains were each inoculated into 4 ml GY medium (2% glucose, 1% yeast extract) and cultured with shaking at 28° C. for 3 or 4 days. The cells were collected by filtration, and RNA was extracted with an RNeasy plant kit (QIAGEN). A SuperScript First-Strand system for RT-PCR (Invitrogen) was used to synthesize cDNA. To confirm expression from the introduced construct and total expression for each gene, RT-PCR was performed with the following primer sets.

Primers Used for Confirmation of Expression from the Introduced Construct:

```
MaGAPDHpfw:
CACACCACACATTCAACATC          (SEQ ID NO: 25)

LPAAT1-r:
GCCTTCGTCCTTGGTACACCTTGAC     (SEQ ID NO: 26)
```

Primers Used for Confirmation of Total LPAAT1 Expression:

```
LPAAT1-2F:
TCGGCTCGGTCCCAAGATGAAC        (SEQ ID NO: 27)

Primer LPAAT1-2R:
GCGTCTGTCATGTGCCCAGTCA        (SEQ ID NO: 28)
```

Based on the results of the above RT-PCR, transformants showing high level expression of each gene both in expression from the introduced construct and in total expression were selected: strains Gp-LPAAT1-long-5 and Gp-LPAAT1-short-6 from those transformed with plasmids pDuraSC-LPAAT1-long and pDuraSC-LPAAT1-short, respectively.

These strains were each inoculated into GY medium (4 ml) and cultured with shaking at 28° C. at 125 rpm. On day 6 of culture, all cells were collected by filtration and lyophilized. A portion (about 10-20 mg) of the dried cells was treated by the hydrochloric acid/methanol method to derive fatty acids in the cells into corresponding methyl esters, followed by extraction with hexane. After distilling off hexane, the fatty acids were analyzed by gas chromatography. Table 5 shows the fatty acid rate in the cells.

TABLE 5

| Ratio (%) of DGLA or arachidonic acid to total fatty acid | | | |
| --- | --- | --- | --- |
| | Gp-LPAAT1-long-5 | Gp-LPAAT1-short-6 | 1S-4 |
| DGLA | 4.15 ± 0.06 | 4.09 ± 0.09 | 3.99 ± 0.18 |
| Arachidonic acid | 43.31 ± 1.44 | 40.28 ± 1.87 | 39.71 ± 1.05 |

As shown above, the *M. alpina* strain transformed to highly express LPAAT1-long or LPAAT1-short was found to show higher ratios of DGLA and arachidonic acid than the wild-type strain 1S-4. Moreover, a comparison was made between the strain transformed to highly express LPAAT1-long and the strain transformed to highly express LPAAT1-short, indicating that this tendency was stronger in the former.

SEQUENCE LISTING FREE TEXT

SEQ ID NO: 6: primer
SEQ ID NO: 7: primer
SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer
SEQ ID NO: 25: primer
SEQ ID NO: 26: primer
SEQ ID NO: 27: primer
SEQ ID NO: 28: primer

---

The invention claimed is:

1. A method for preparing a fatty acid composition, which comprises collecting a fatty acid composition from a cultured microorganism transformed with a recombinant vector carrying a nucleic acid comprising a nucleotide sequence shown in any one of (a) to (c) below:
(a) a nucleotide sequence which encodes a protein consisting of an amino acid sequence with deletion, substitution or addition of one to twenty amino acids in the amino acid sequence shown in SEQ ID NO: 2 and having lysophosphatidic acid acyltransferase activity;
(b) a nucleotide sequence which consists of a nucleotide sequence sharing an identity of 95% or more with the nucleotide sequence consisting of SEQ ID NO: 1 and which encodes a protein having lysophosphatidic acid acyltransferase activity; or
(c) a nucleotide sequence which encodes an amino acid sequence sharing an identity of 95% or more with the amino acid sequence consisting of SEQ ID NO: 2 and having lysophosphatidic acid acyltransferase activity.

2. The method according to claim 1, wherein the fatty acid composition comprises an n-6 fatty acid, oleic acid, palmitic acid, stearic acid, or palmitoleic acid.

3. The method according to claim 1, wherein the nucleic acid comprises a nucleotide sequence shown in (a) or (b) below:
(a) a nucleotide sequence which encodes a protein consisting of an amino acid sequence with deletion, substitution or addition of 1 to 10 amino acids in the amino acid sequence shown in SEQ ID NO: 2 and having lysophosphatidic acid acyltransferase activity; or
(b) a nucleotide sequence which encodes an amino acid sequence sharing an identity of 95% or more with the amino acid sequence consisting of SEQ ID NO: 2 and having lysophosphatidic acid acyltransferase activity.

4. The method according to claim 2, wherein the nucleic acid comprises a nucleotide sequence shown in (a) to or (b) below:
(a) a nucleotide sequence which encodes a protein consisting of an amino acid sequence with deletion, substitution or addition of 1 to 10 amino acids in the amino acid sequence shown in SEQ ID NO: 2 and having lysophosphatidic acid acyltransferase activity; or
(b) a nucleotide sequence which encodes an amino acid sequence sharing an identity of 95% or more with the amino acid sequence consisting of SEQ ID NO: 2 and having lysophosphatidic acid acyltransferase activity.

5. The method according to claim 1, wherein the microorganism is selected from a group consisting of yeast, arachidonic acid-producing yeast, *M. alpina*, filamentous fungi, *E. coli*, and *Bacillus subtilis*.

6. The method according to claim 1, which comprises collecting the fatty acid composition from the cultured microorganism by lyophilization of the microorganisms followed by solubilization and extraction with an organic solvent.

* * * * *

SEQUENCE LISTING

<160> NUMBER OF SEQ ID NOS: 32

<210> SEQ ID NO 1
<211> LENGTH: 1443
<212> TYPE: DNA
<213> ORGANISM: Mortierella alpina
<220> FEATURE:
<221> NAME/KEY: CDS
<222> LOCATION: (1)..(1443)

<400> SEQUENCE: 1

```
atg act gtc gca aag ctg gac cct gga acc acc agt cct atc tca ccc      48
Met Thr Val Ala Lys Leu Asp Pro Gly Thr Thr Ser Pro Ile Ser Pro
1               5                   10                  15 tcg gcc tcg gcc tcg ttt tcg ccc ccg acc acc cct ctc tcg cag aag      96
Ser Ala Ser Ala Ser Phe Ser Pro Pro Thr Thr Pro Leu Ser Gln Lys
            20                  25                  30 aag ggt atc tac tcg gcg act acc act tct acc act acc acc act         144
Lys Gly Ile Tyr Ser Ala Thr Thr Thr Ser Thr Thr Thr Thr Thr
        35                  40                  45 acc acc acc aaa atc tcg agc tct agc aac tct tct agc gca acg ctc     192
Thr Thr Thr Lys Ile Ser Ser Ser Ser Asn Ser Ser Ser Ala Thr Leu
50                  55                  60 atg gat gaa tcc acc acc acc cac cac aca gag acc agc agc aag         240
Met Asp Glu Ser Thr Thr Thr Thr His His Thr Glu Thr Ser Ser Lys
65                  70                  75                  80 acg tcc tcg cac ccc cgt cgg ctc ggt ccc aag atg aac ccc atc tac     288
Thr Ser Ser His Pro Arg Arg Leu Gly Pro Lys Met Asn Pro Ile Tyr
                85                  90                  95 aag ggt ctg cga gcc ttt gtc tgg gcc ttg tac ttc aac cta gga gca     336
Lys Gly Leu Arg Ala Phe Val Trp Ala Leu Tyr Phe Asn Leu Gly Ala
            100                 105                 110 tct ctc ata tcg ata acc caa gtc ctg tcg ttg cct ctg gcg ttg atc     384
Ser Leu Ile Ser Ile Thr Gln Val Leu Ser Leu Pro Leu Ala Leu Ile
        115                 120                 125 gct cca aaa gtt tac cag tgg cac atc act aaa acc cag ggt cac ttt     432
Ala Pro Lys Val Tyr Gln Trp His Ile Thr Lys Thr Gln Gly His Phe
    130                 135                 140 ggg gct ttc ctg ctc aag atg aac cag cta ttt gcg ccc tca gat atc     480
Gly Ala Phe Leu Leu Lys Met Asn Gln Leu Phe Ala Pro Ser Asp Ile
145                 150                 155                 160 gtc ttg acg gga gat gaa agt gtc agg gga atc gtc aag gtg tac caa     528
Val Leu Thr Gly Asp Glu Ser Val Arg Gly Ile Val Lys Val Tyr Gln
                165                 170                 175 gga cga agg ctg aag gac act ggt gag gcg tac agc ggt cat gga gag     576
Gly Arg Arg Leu Lys Asp Thr Gly Glu Ala Tyr Ser Gly His Gly Glu
            180                 185                 190 gac att att ctg gat atg ccc gag agg atg gtt ttc atc gcg aac cac     624
Asp Ile Ile Leu Asp Met Pro Glu Arg Met Val Phe Ile Ala Asn His
        195                 200                 205 cag atc tat tct gac tgg atg tac ctc tgg tgc ttc tcc tat ttc gca     672
```

```
Gln Ile Tyr Ser Asp Trp Met Tyr Leu Trp Cys Phe Ser Tyr Phe Ala
    210                 215                 220 gag agg cac agg gca ctg aag att att ctt cgg ggc gac ctg acc tgg      720
Glu Arg His Arg Ala Leu Lys Ile Ile Leu Arg Gly Asp Leu Thr Trp
225                 230                 235                 240 atc cct gtc ttt ggc tgg ggt atg cgg ttc ttt gac ttt atc ttt ttg      768
Ile Pro Val Phe Gly Trp Gly Met Arg Phe Phe Asp Phe Ile Phe Leu
                245                 250                 255 aaa cgt aat gac tgg gca cat gac aga cgc gcc att gag gag aac ctg      816
Lys Arg Asn Asp Trp Ala His Asp Arg Arg Ala Ile Glu Glu Asn Leu
            260                 265                 270 gga cgt gtc aag gaa aag gat cca ctc tgg ctg gta gtc ttc cct gaa      864
Gly Arg Val Lys Glu Lys Asp Pro Leu Trp Leu Val Val Phe Pro Glu
        275                 280                 285 gga aca gtc gtc tcc aag gaa acg cgt ttg cga tct gtt gcc ttt tca      912
Gly Thr Val Val Ser Lys Glu Thr Arg Leu Arg Ser Val Ala Phe Ser
    290                 295                 300 aag aag gct ggt ctt tcg gat cac cgc cat gtg ttg ctt cca aga acc      960
Lys Lys Ala Gly Leu Ser Asp His Arg His Val Leu Leu Pro Arg Thr
305                 310                 315                 320 agc ggc ctc ttt gtt tgc atc aac aag ttg cgt gga tcc gtc gaa tac     1008
Ser Gly Leu Phe Val Cys Ile Asn Lys Leu Arg Gly Ser Val Glu Tyr
                325                 330                 335 tta tac gac gcg aca gtt ggc tac tcg aac gtt gaa tat gga gag att     1056
Leu Tyr Asp Ala Thr Val Gly Tyr Ser Asn Val Glu Tyr Gly Glu Ile
            340                 345                 350 cca cag gag ctt tac cct ttg cca ggg cta tat atc aac aag gcg cag     1104
Pro Gln Glu Leu Tyr Pro Leu Pro Gly Leu Tyr Ile Asn Lys Ala Gln
        355                 360                 365 ccc aag gag atc aac atg cac ctg cgg cgg ttt gct atc aag gat atc     1152
Pro Lys Glu Ile Asn Met His Leu Arg Arg Phe Ala Ile Lys Asp Ile
    370                 375                 380 ccc acg tca gaa ccc gag ttt gtg gag tgg gtc cga gcg cgg tgg gta     1200
Pro Thr Ser Glu Pro Glu Phe Val Glu Trp Val Arg Ala Arg Trp Val
385                 390                 395                 400 gag aag gat gag ctg atg gag gag ttt tat acc aag ggc cga ttc cca     1248
Glu Lys Asp Glu Leu Met Glu Glu Phe Tyr Thr Lys Gly Arg Phe Pro
                405                 410                 415 tcg cag ctg acg gct gag gac att ggc gag aag gag acc aac aag gca     1296
Ser Gln Leu Thr Ala Glu Asp Ile Gly Glu Lys Glu Thr Asn Lys Ala
            420                 425                 430 gga ggc tca tct gaa gga cag agt gtc aga atc ccg ctc aaa tcg cga     1344
Gly Gly Ser Ser Glu Gly Gln Ser Val Arg Ile Pro Leu Lys Ser Arg
        435                 440                 445 ggc atg atg gac tac ctc atg cct tcg gcc att aac ctg gtt gcg ctg     1392
Gly Met Met Asp Tyr Leu Met Pro Ser Ala Ile Asn Leu Val Ala Leu
    450                 455                 460 cca gta ctg gct ttt gcg atg aga tat gct ctg cag caa gta tcg tct     1440
Pro Val Leu Ala Phe Ala Met Arg Tyr Ala Leu Gln Gln Val Ser Ser
465                 470                 475                 480 ggt                                                                  1443
Gly

<210> SEQ ID NO 2
<211> LENGTH: 481
<212> TYPE: PRT
<213> ORGANISM: Mortierella alpina

<400> SEQUENCE: 2

Met Thr Val Ala Lys Leu Asp Pro Gly Thr Thr Ser Pro Ile Ser Pro
1               5                   10                  15
```

```
Ser Ala Ser Ala Ser Phe Ser Pro Pro Thr Thr Pro Leu Ser Gln Lys
         20                  25                  30

Lys Gly Ile Tyr Ser Ala Thr Thr Thr Ser Thr Thr Thr Thr Thr Thr
             35                  40                  45

Thr Thr Thr Lys Ile Ser Ser Ser Asn Ser Ser Ser Ala Thr Leu
     50                  55                  60

Met Asp Glu Ser Thr Thr Thr Thr His His Thr Glu Thr Ser Ser Lys
65                      70                  75                  80

Thr Ser Ser His Pro Arg Arg Leu Gly Pro Lys Met Asn Pro Ile Tyr
                 85                  90                  95

Lys Gly Leu Arg Ala Phe Val Trp Ala Leu Tyr Phe Asn Leu Gly Ala
             100                 105                 110

Ser Leu Ile Ser Ile Thr Gln Val Leu Ser Leu Pro Leu Ala Leu Ile
             115                 120                 125

Ala Pro Lys Val Tyr Gln Trp His Ile Thr Lys Thr Gln Gly His Phe
         130                 135                 140

Gly Ala Phe Leu Leu Lys Met Asn Gln Leu Phe Ala Pro Ser Asp Ile
145                 150                 155                 160

Val Leu Thr Gly Asp Glu Ser Val Arg Gly Ile Val Lys Val Tyr Gln
             165                 170                 175

Gly Arg Arg Leu Lys Asp Thr Gly Glu Ala Tyr Ser Gly His Gly Glu
             180                 185                 190

Asp Ile Ile Leu Asp Met Pro Glu Arg Met Val Phe Ile Ala Asn His
             195                 200                 205

Gln Ile Tyr Ser Asp Trp Met Tyr Leu Trp Cys Phe Ser Tyr Phe Ala
         210                 215                 220

Glu Arg His Arg Ala Leu Lys Ile Ile Leu Arg Gly Asp Leu Thr Trp
225                 230                 235                 240

Ile Pro Val Phe Gly Trp Gly Met Arg Phe Phe Asp Phe Ile Phe Leu
             245                 250                 255

Lys Arg Asn Asp Trp Ala His Asp Arg Arg Ala Ile Glu Glu Asn Leu
             260                 265                 270

Gly Arg Val Lys Glu Lys Asp Pro Leu Trp Leu Val Val Phe Pro Glu
             275                 280                 285

Gly Thr Val Val Ser Lys Glu Thr Arg Leu Arg Ser Val Ala Phe Ser
         290                 295                 300

Lys Lys Ala Gly Leu Ser Asp His Arg His Val Leu Leu Pro Arg Thr
305                 310                 315                 320

Ser Gly Leu Phe Val Cys Ile Asn Lys Leu Arg Gly Ser Val Glu Tyr
                 325                 330                 335

Leu Tyr Asp Ala Thr Val Gly Tyr Ser Asn Val Glu Tyr Gly Glu Ile
             340                 345                 350

Pro Gln Glu Leu Tyr Pro Leu Pro Gly Leu Tyr Ile Asn Lys Ala Gln
         355                 360                 365

Pro Lys Glu Ile Asn Met His Leu Arg Arg Phe Ala Ile Lys Asp Ile
         370                 375                 380

Pro Thr Ser Glu Pro Glu Phe Val Glu Trp Val Arg Ala Arg Trp Val
385                 390                 395                 400

Glu Lys Asp Glu Leu Met Glu Glu Phe Tyr Thr Lys Gly Arg Phe Pro
                 405                 410                 415

Ser Gln Leu Thr Ala Glu Asp Ile Gly Glu Lys Glu Thr Asn Lys Ala
             420                 425                 430

Gly Gly Ser Ser Glu Gly Gln Ser Val Arg Ile Pro Leu Lys Ser Arg
```

```
                435               440              445
Gly Met Met Asp Tyr Leu Met Pro Ser Ala Ile Asn Leu Val Ala Leu
            450                  455                 460

Pro Val Leu Ala Phe Ala Met Arg Tyr Ala Leu Gln Gln Val Ser Ser
465                 470                 475                 480

Gly

<210> SEQ ID NO 3
<211> LENGTH: 1627
<212> TYPE: DNA
<213> ORGANISM: Mortierella alpina

<400> SEQUENCE: 3
gctcttccct ctcttcccgc tctactctca cttctcgctc gtcttcccca ccctctcacc      60
cattcgcaga gaacaagtgt gcctgctgca cccacacgga tatgactgtc gcaaagctgg    120
accctggaac caccagtcct atctcaccct cggcctcggc ctcgttttcg ccccgacca     180 cccctctctc gcagaagaag ggtatctact cggcgactac cacttctacc actaccacca    240
ccactaccac caccaaaatc tcgagctcta gcaactcttc tagcgcaacg ctcatggatg    300
aatccaccac caccacccac cacacagaga ccagcagcaa gacgtcctcg cacccccgtc    360
ggctcggtcc caagatgaac cccatctaca agggtctgcg agcctttgtc tgggccttgt    420
acttcaacct aggagcatct ctcatatcga taacccaagt cctgtcgttg cctctggcgt    480
tgatcgctcc aaaagtttac cagtggcaca tcactaaaac ccagggtcac tttgggctt    540 tcctgctcaa gatgaaccag ctatttgcgc cctcagatat cgtcttgacg ggagatgaaa    600
gtgtcagggg aatcgtcaag gtgtaccaag gacgaaggct gaaggacact ggtgaggcgt    660
acagcggtca tggagaggac attattctgg atatgcccga gaggatggtt ttcatcgcga    720
accaccagat ctattctgac tggatgtacc tctggtgctt ctcctatttc gcagagaggc    780
acagggcact gaagattatt cttcggggcg acctgacctg gatccctgtc tttggctggg    840
gtatgcggtt ctttgacttt atcttttga aacgtaatga ctgggcacat gacagacgcg    900
ccattgagga gaacctggga cgtgtcaagg aaaaggatcc actctggctg gtagtcttcc    960
ctgaaggaac agtcgtctcc aaggaaacgc gtttgcgatc tgttgccttt tcaaagaagg   1020
ctggtctttc ggatcaccgc catgtgttgc ttccaagaac cagcggcctc tttgtttgca   1080
tcaacaagtt gcgtggatcc gtcgaatact tatacgacgc gacagttggc tactcgaacg   1140
ttgaatatgg agagattcca caggagcttt acccctttgcc agggctatat atcaacaagg   1200
cgcagcccaa ggagatcaac atgcacctgc ggcggtttgc tatcaaggat atccccacgt   1260
cagaacccga gtttgtggag tgggtccgag cgcggtgggt agagaaggat gagctgatgg   1320
aggagtttta taccaagggc cgattcccat cgcagctgac ggctgaggac attggcgaga   1380
aggagaccaa caaggcagga ggctcatctg aaggacagag tgtcagaatc ccgctcaaat   1440
cgcgaggcat gatggactac ctcatgcctt cggccattaa cctggttgcg ctgccagtac   1500
tggcttttgc gatgagatat gctctgcagc aagtatcgtc tggttgattt attttttgtt   1560
agacgctgcc gtagttgtaa atttgatgag tgctatttag agcaaacgaa agaagagact   1620
taaacgc                                                            1627

<210> SEQ ID NO 4
<211> LENGTH: 1446
<212> TYPE: DNA
<213> ORGANISM: Mortierella alpina
```

-continued

```
<400> SEQUENCE: 4
atgactgtcg caaagctgga ccctggaacc accagtccta tctcaccctc ggcctcggcc    60
tcgttttcgc ccccgaccac ccctctctcg cagaagaagg gtatctactc ggcgactacc   120
acttctacca ctaccaccac cactaccacc accaaaatct cgagctctag caactcttct   180
agcgcaacgc tcatggatga atccaccacc accacccacc acacagagac cagcagcaag   240
acgtcctcgc accccgtcg gctcggtccc aagatgaacc ccatctacaa gggtctgcga    300
gcctttgtct gggccttgta cttcaaccta ggagcatctc tcatatcgat aacccaagtc   360
ctgtcgttgc ctctggcgtt gatcgctcca aaagtttacc agtggcacat cactaaaacc   420
cagggtcact ttggggcttt cctgctcaag atgaaccagc tatttgcgcc ctcagatatc   480
gtcttgacgg gagatgaaag tgtcagggga tcgtcaagg tgtaccaagg acgaaggctg    540
aaggacactg gtgaggcgta cagcggtcat ggagaggaca ttattctgga tatgcccgag   600
aggatggttt tcatcgcgaa ccaccagatc tattctgact ggatgtacct ctggtgcttc   660
tcctatttcg cagagaggca cagggcactg aagattattc ttcggggcga cctgacctgg   720
atccctgtct ttggctgggg tatgcggttc tttgactta tcttttgaa cgtaatgac     780 tgggcacatg acagacgcgc cattgaggag aacctgggac gtgtcaagga aaaggatcca   840
ctctggctgg tagtcttccc tgaaggaaca gtcgtctcca aggaaacgcg tttgcgatct   900
gttgcctttt caagaaggc tggtctttcg gatcaccgcc atgtgttgct tccaagaacc    960
agcggcctct ttgtttgcat caacaagttg cgtggatccg tcgaatactt atacgacgcg  1020
acagttggct actcgaacgt tgaatatgga gagattccac aggagcttta ccctttgcca  1080
gggctatata tcaacaaggc gcagcccaag gagatcaaca tgcacctgcg gcggtttgct  1140
atcaaggata tccccacgtc agaacccgag tttgtggagt gggtccgagc gcggtgggta  1200
gagaaggatg agctgatgga ggagttttat accaagggcc gattcccatc gcagctgacg  1260
gctgaggaca ttggcgagaa ggagaccaac aaggcaggag gctcatctga aggacagagt  1320
gtcagaatcc cgctcaaatc gcgaggcatg atggactacc tcatgccttc ggccattaac  1380
ctggttgcgc tgccagtact ggcttttgcg atgagatatg ctctgcagca agtatcgtct  1440
ggttga                                                            1446

<210> SEQ ID NO 5
<211> LENGTH: 843
<212> TYPE: DNA
<213> ORGANISM: Mortierella alpina
<220> FEATURE:
<221> NAME/KEY: modified_base
<222> LOCATION: (793)..(793)
<223> OTHER INFORMATION: a, c, t, g, unknown or other

<400> SEQUENCE: 5
gcgccattga ggagaacctg gacgtgtca aggaaaagga tccactctgg ctggtagtct    60
tccctgaagg aacagtcgtc tccaaggaaa cgcgtttgcg atctgttgcc ttttcaaaga   120
aggctggtct ttcggatcac cgccatgtgt tgcttccaag aaccagcggc ctctttgttt   180
gcatcaacaa gttgcgtgga tccgtcgaat acttatacga cgcgacagtt ggctactcga   240
acgttgaata tggagagatt ccacaggagc tttacccttt gccagggcta tatatcaaca   300
aggcgcagcc caaggagatc aacatgcacc tgcggcggtt tgctatcaag gatatcccca   360
cgtcagaacc cgagtttgtg gagtgggtcc gagcgcggtg ggtagagaag gatgagctga   420
tggaggagtt ttataccaag ggccgattcc catcgcagct gacggctgag gacattggcg   480
```

| | | |
|---|---|---|
| agaaggagac caacaaggca ggaggctcat ctgaaggaca gagtgtcaga atcccgctca | 540 |
| aatcgcgagg catgatggac tacctcatgc cttcggccat taacctggtt gcgctgccag | 600 |
| tactggcttt tgcgatgaga tatgctctgc agcaagtatc gtctggttga tttattttt | 660 |
| gttagacgct gccgtagttg taaatttgat gagtgctatt tagagcaaac gaaagaagag | 720 |
| acttaaacgc atggatgtgt gtaatttcat aacagaaaaa aaaaaaaaaa aaaaaaaaa | 780 |
| aacctgcagc ccnggggat ccactagttc tagagcgccg ccaccgcggt ggagctcagc | 840 |
| gtt | 843 |

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggacgtgtca aggaaaagga                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccttcagat gagcctcctg                                           20

<210> SEQ ID NO 8
<211> LENGTH: 1251
<212> TYPE: DNA
<213> ORGANISM: Mortierella alpina

<400> SEQUENCE: 8

| | | |
|---|---|---|
| atggatgaat ccaccaccac cacccaccac acagagacca gcagcaagac gtcctcgcac | 60 |
| ccccgtcggc tcggtcccaa gatgaacccc atctacaagg gtctgcgagc ctttgtctgg | 120 |
| gccttgtact tcaacctagg agcatctctc atatcgataa cccaagtcct gtcgttgcct | 180 |
| ctggcgttga tcgctccaaa agtttaccag tggcacatca ctaaaaccca gggtcacttt | 240 |
| ggggctttcc tgctcaagat gaaccagcta tttgcgccct cagatatcgt cttgacggga | 300 |
| gatgaaagtg tcaggggaat cgtcaaggtg taccaaggac gaaggctgaa ggacactggt | 360 |
| gaggcgtaca gcggtcatgg agaggacatt attctgata tgcccgagag gatggttttc | 420 |
| atcgcgaacc accagatcta ttctgactgg atgtacctct ggtgcttctc ctatttcgca | 480 |
| gagaggcaca gggcactgaa gattattctt cggggcgacc tgacctggat ccctgtcttt | 540 |
| ggctggggta tgcggttctt tgactttatc tttttgaaac gtaatgactg gcacatgac | 600 |
| agacgcgcca ttgaggagaa cctgggacgt gtcaaggaaa aggatccact ctggctggta | 660 |
| gtcttccctg aaggaacagt cgtctccaag gaaacgcgtt tgcgatctgt tgccttttca | 720 |
| aagaaggctg tcttttcgga tcaccgccat gtgttgcttc caagaaccag cggcctcttt | 780 |
| gtttgcatca acaagttgcg tggatccgtc gaatacttat acgacgcgac agttggctac | 840 |
| tcgaacgttg aatatggaga gattccacag gagcttacc ctttgccagg gctatatatc | 900 |
| aacaaggcgc agcccaagga gatcaacatg cacctgcggc ggtttgctat caaggatatc | 960 |

```
cccacgtcag aacccgagtt tgtggagtgg gtccgagcgc ggtgggtaga gaaggatgag    1020
ctgatggagg agtttatac caagggccga ttcccatcgc agctgacggc tgaggacatt     1080
ggcgagaagg agaccaacaa ggcaggaggc tcatctgaag acagagtgt cagaatcccg    1140 ctcaaatcgc gaggcatgat ggactacctc atgccttcgg ccattaacct ggttgcgctg    1200
ccagtactgg cttttgcgat gagatatgct ctgcagcaag tatcgtctgg t            1251

<210> SEQ ID NO 9
<211> LENGTH: 1369
<212> TYPE: DNA
<213> ORGANISM: Mortierella alpina
<220> FEATURE:
<221> NAME/KEY: CDS
<222> LOCATION: (36)..(1286)

<400> SEQUENCE: 9
```

```
tctcgagctc tagcaactct tctagcgcaa cgctc atg gat gaa tcc acc acc              53
                                     Met Asp Glu Ser Thr Thr
                                     1               5 acc acc cac cac aca gag acc agc agc aag acg tcc tcg cac ccc cgt           101
Thr Thr His His Thr Glu Thr Ser Ser Lys Thr Ser Ser His Pro Arg
            10                  15                  20 cgg ctc ggt ccc aag atg aac ccc atc tac aag ggt ctg cga gcc ttt           149
Arg Leu Gly Pro Lys Met Asn Pro Ile Tyr Lys Gly Leu Arg Ala Phe
        25                  30                  35 gtc tgg gcc ttg tac ttc aac cta gga gca tct ctc ata tcg ata acc           197
Val Trp Ala Leu Tyr Phe Asn Leu Gly Ala Ser Leu Ile Ser Ile Thr
    40                  45                  50 caa gtc ctg tcg ttg cct ctg gcg ttg atc gct cca aaa gtt tac cag           245
Gln Val Leu Ser Leu Pro Leu Ala Leu Ile Ala Pro Lys Val Tyr Gln
55                  60                  65                  70 tgg cac atc act aaa acc cag ggt cac ttt ggg gct ttc ctg ctc aag           293
Trp His Ile Thr Lys Thr Gln Gly His Phe Gly Ala Phe Leu Leu Lys
                75                  80                  85 atg aac cag cta ttt gcg ccc tca gat atc gtc ttg acg gga gat gaa           341
Met Asn Gln Leu Phe Ala Pro Ser Asp Ile Val Leu Thr Gly Asp Glu
            90                  95                 100 agt gtc agg gga atc gtc aag gtg tac caa gga cga agg ctg aag gac           389
Ser Val Arg Gly Ile Val Lys Val Tyr Gln Gly Arg Arg Leu Lys Asp
        105                 110                 115 act ggt gag gcg tac agc ggt cat gga gag gac att att ctg gat atg           437
Thr Gly Glu Ala Tyr Ser Gly His Gly Glu Asp Ile Ile Leu Asp Met
    120                 125                 130 ccc gag agg atg gtt ttc atc gcg aac cac cag atc tat tct gac tgg           485
Pro Glu Arg Met Val Phe Ile Ala Asn His Gln Ile Tyr Ser Asp Trp
135                 140                 145                 150 atg tac ctc tgg tgc ttc tcc tat ttc gca gag agg cac agg gca ctg           533
Met Tyr Leu Trp Cys Phe Ser Tyr Phe Ala Glu Arg His Arg Ala Leu
                155                 160                 165 aag att att ctt cgg ggc gac ctg acc tgg atc cct gtc ttt ggc tgg           581
Lys Ile Ile Leu Arg Gly Asp Leu Thr Trp Ile Pro Val Phe Gly Trp
            170                 175                 180 ggt atg cgg ttc ttt gac ttt atc ttt ttg aaa cgt aat gac tgg gca           629
Gly Met Arg Phe Phe Asp Phe Ile Phe Leu Lys Arg Asn Asp Trp Ala
        185                 190                 195 cat gac aga cgc gcc att gag gag aac ctg gga cgt gtc aag gaa aag           677
His Asp Arg Arg Ala Ile Glu Glu Asn Leu Gly Arg Val Lys Glu Lys
    200                 205                 210 gat cca ctc tgg ctg gta gtc ttc cct gaa gga aca gtc gtc tcc aag           725
Asp Pro Leu Trp Leu Val Val Phe Pro Glu Gly Thr Val Val Ser Lys
215                 220                 225                 230
```

```
gaa acg cgt ttg cga tct gtt gcc ttt tca aag aag gct ggt ctt tcg      773
Glu Thr Arg Leu Arg Ser Val Ala Phe Ser Lys Lys Ala Gly Leu Ser
                235                 240                 245 gat cac cgc cat gtg ttg ctt cca aga acc agc ggc ctc ttt gtt tgc      821
Asp His Arg His Val Leu Leu Pro Arg Thr Ser Gly Leu Phe Val Cys
            250                 255                 260 atc aac aag ttg cgt gga tcc gtc gaa tac tta tac gac gcg aca gtt      869
Ile Asn Lys Leu Arg Gly Ser Val Glu Tyr Leu Tyr Asp Ala Thr Val
        265                 270                 275 ggc tac tcg aac gtt gaa tat gga gag att cca cag gag ctt tac cct      917
Gly Tyr Ser Asn Val Glu Tyr Gly Glu Ile Pro Gln Glu Leu Tyr Pro
    280                 285                 290 ttg cca ggg cta tat atc aac aag gcg cag ccc aag gag atc aac atg      965
Leu Pro Gly Leu Tyr Ile Asn Lys Ala Gln Pro Lys Glu Ile Asn Met
295                 300                 305                 310 cac ctg cgg cgg ttt gct atc aag gat atc ccc acg tca gaa ccc gag     1013
His Leu Arg Arg Phe Ala Ile Lys Asp Ile Pro Thr Ser Glu Pro Glu
                315                 320                 325 ttt gtg gag tgg gtc cga gcg cgg tgg gta gag aag gat gag ctg atg     1061
Phe Val Glu Trp Val Arg Ala Arg Trp Val Glu Lys Asp Glu Leu Met
            330                 335                 340 gag gag ttt tat acc aag ggc cga ttc cca tcg cag ctg acg gct gag     1109
Glu Glu Phe Tyr Thr Lys Gly Arg Phe Pro Ser Gln Leu Thr Ala Glu
        345                 350                 355 gac att ggc gag aag gag acc aac aag gca gga ggc tca tct gaa gga     1157
Asp Ile Gly Glu Lys Glu Thr Asn Lys Ala Gly Gly Ser Ser Glu Gly
    360                 365                 370 cag agt gtc aga atc ccg ctc aaa tcg cga ggc atg atg gac tac ctc     1205
Gln Ser Val Arg Ile Pro Leu Lys Ser Arg Gly Met Met Asp Tyr Leu
375                 380                 385                 390 atg cct tcg gcc att aac ctg gtt gcg ctg cca gta ctg gct ttt gcg     1253
Met Pro Ser Ala Ile Asn Leu Val Ala Leu Pro Val Leu Ala Phe Ala
                395                 400                 405 atg aga tat gct ctg cag caa gta tcg tct ggt tgatttattt tttgttagac   1306
Met Arg Tyr Ala Leu Gln Gln Val Ser Ser Gly
            410                 415 gctgccgtag ttgtaaattt gatgagtgct atttagagca aacgaaagaa gagacttaaa   1366
cgc                                                                 1369

<210> SEQ ID NO 10
<211> LENGTH: 417
<212> TYPE: PRT
<213> ORGANISM: Mortierella alpina

<400> SEQUENCE: 10

Met Asp Glu Ser Thr Thr Thr Thr His His Thr Glu Thr Ser Ser Lys
1               5                   10                  15

Thr Ser Ser His Pro Arg Arg Leu Gly Pro Lys Met Asn Pro Ile Tyr
            20                  25                  30

Lys Gly Leu Arg Ala Phe Val Trp Ala Leu Tyr Phe Asn Leu Gly Ala
        35                  40                  45

Ser Leu Ile Ser Ile Thr Gln Val Leu Ser Leu Pro Leu Ala Leu Ile
    50                  55                  60

Ala Pro Lys Val Tyr Gln Trp His Ile Thr Lys Thr Gln Gly His Phe
65                  70                  75                  80

Gly Ala Phe Leu Leu Lys Met Asn Gln Leu Phe Ala Pro Ser Asp Ile
                85                  90                  95

Val Leu Thr Gly Asp Glu Ser Val Arg Gly Ile Val Lys Val Tyr Gln
```

```
            100                 105                 110
Gly Arg Arg Leu Lys Asp Thr Gly Glu Ala Tyr Ser Gly His Gly Glu
            115                 120                 125

Asp Ile Ile Leu Asp Met Pro Glu Arg Met Val Phe Ile Ala Asn His
            130                 135                 140

Gln Ile Tyr Ser Asp Trp Met Tyr Leu Trp Cys Phe Ser Tyr Phe Ala
145                 150                 155                 160

Glu Arg His Arg Ala Leu Lys Ile Ile Leu Arg Gly Asp Leu Thr Trp
                165                 170                 175

Ile Pro Val Phe Gly Trp Gly Met Arg Phe Phe Asp Phe Ile Phe Leu
            180                 185                 190

Lys Arg Asn Asp Trp Ala His Asp Arg Arg Ala Ile Glu Glu Asn Leu
            195                 200                 205

Gly Arg Val Lys Glu Lys Asp Pro Leu Trp Leu Val Val Phe Pro Glu
            210                 215                 220

Gly Thr Val Val Ser Lys Glu Thr Arg Leu Arg Ser Val Ala Phe Ser
225                 230                 235                 240

Lys Lys Ala Gly Leu Ser Asp His Arg His Val Leu Leu Pro Arg Thr
                245                 250                 255

Ser Gly Leu Phe Val Cys Ile Asn Lys Leu Arg Gly Ser Val Glu Tyr
            260                 265                 270

Leu Tyr Asp Ala Thr Val Gly Tyr Ser Asn Val Glu Tyr Gly Glu Ile
            275                 280                 285

Pro Gln Glu Leu Tyr Pro Leu Pro Gly Leu Tyr Ile Asn Lys Ala Gln
            290                 295                 300

Pro Lys Glu Ile Asn Met His Leu Arg Arg Phe Ala Ile Lys Asp Ile
305                 310                 315                 320

Pro Thr Ser Glu Pro Glu Phe Val Glu Trp Val Arg Ala Arg Trp Val
                325                 330                 335

Glu Lys Asp Glu Leu Met Glu Glu Phe Tyr Thr Lys Gly Arg Phe Pro
            340                 345                 350

Ser Gln Leu Thr Ala Glu Asp Ile Gly Glu Lys Glu Thr Asn Lys Ala
            355                 360                 365

Gly Gly Ser Ser Glu Gly Gln Ser Val Arg Ile Pro Leu Lys Ser Arg
            370                 375                 380

Gly Met Met Asp Tyr Leu Met Pro Ser Ala Ile Asn Leu Val Ala Leu
385                 390                 395                 400

Pro Val Leu Ala Phe Ala Met Arg Tyr Ala Leu Gln Gln Val Ser Ser
                405                 410                 415

Gly
```

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctgagatgg atgaatccac caccaccac                                    29

<210> SEQ ID NO 12
<211> LENGTH: 32
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 12
gtcgactcaa ccagacgata cttgctgcag ag                                    32

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctagaatgg cacctcccaa cactattg                                         28

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagcttttac ttcttgaaaa agaccacgtc                                       30

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctagaatgg ctgctgctcc cagtgtgag                                        29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagcttttac tgtgccttgc ccatcttgg                                        29

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tctagaatgg agtcgattgc gcaattcc                                         28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gagctcttac tgcaacttcc ttgccttctc                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctagaatgg gtgcggacac aggaaaaacc                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aagcttttac tcttccttgg gacgaagacc                                    30

<210> SEQ ID NO 21
<211> LENGTH: 1203
<212> TYPE: DNA
<213> ORGANISM: Mortierella alpina

<400> SEQUENCE: 21
atggcacctc ccaacactat tgatgccggt ttgacccagc gccatatcag cacctcggcc    60
gccccaacct ctgccaagcc cgccttcgag cgcaactacc agctccctga gttcaccatc   120
aaggagatcc gtgagtgcat ccctgcacac tgctttgagc gctccggtct ccgtggtctt   180
tgccacgttg ctattgatct gacctgggcc tcgctcttgt tcctggctgc gacccagatc   240
gacaagttcg agaacccttt gatccgctac ttggcctggc ctgcgtattg gatcatgcag   300
ggtattgttt gcaccggtat ctgggtattg gcacacgaat gtggtcatca gtccttctcg   360
acctccaaga cccttaacaa cactgtcggc tggatcttgc actcgatgct cttggtccct   420
taccactcct ggagaatctc gcactcgaag caccacaagg ccactggcca catgaccaag   480
gaccaggtct tgttcccaa gaccgctct caggttggct tgccccccaa ggagaatgtt   540
gcagttgccg ttcaggagga ggatatgtcc gtgcacctgg atgaggaggc ccccattgtg   600
actttgttct ggatggtgat tcagttcctg ttcggatggc ctgcgtacct tattatgaac   660
gcctctggtc aagactatgg ccgctggacc tcgcacttcc acacctactc tcctatcttt   720
gagccccgca acttttttcga cattatcatt tcggatctcg gtgtgttggc tgctcttggt   780
accttgatct acgcctccat gcagctctcg ctcttgaccg tgaccaagta ctacattgtc   840
ccctacttgt tgtcaacttt ctggttggtc ctgatcacct tcttgcagca caccgaccct   900
aagctgcccc attaccgtga gggtgcctgg aacttccagc gtggagccct ctgcaccgtt   960
gaccgctcgt tcggcaagtt cttggaccat atgttccacg gcattgtcca tacccatgta  1020
gcccatcact tgttctcgca gatgccgttc taccatgctg aggaagccac ccatcatctc  1080
aagaaactgc tgggagagta ctacgtctat gacccatcgc cgattgttgt tgcggtctgg  1140
aggtcgttcc gtgaatgccg attcgtggaa gaccatggag acgtggtctt tttcaagaag  1200
taa                                                                1203

<210> SEQ ID NO 22
<211> LENGTH: 1374
<212> TYPE: DNA
<213> ORGANISM: Mortierella alpina

<400> SEQUENCE: 22

```
atggctgctg ctcccagtgt gaggacgttt actcgggccg agattttgaa tgccgaggcc      60
ctgaatgagg gcaagaagga tgccgaggca cccttctga tgatcattga caacaaggtg     120
tacgatgtcc gcgagtttgt ccctgatcat cccggtggaa gtgtgattct cacgcacgtt     180
ggcaaggacg gcactgacgt ctttgacact ttccaccccg aggctgcttg ggagactctt     240
gccaactttt acgttggtga tattgatgag agcgatcgtg ccatcaagaa tgatgacttt     300
gcggccgagg ttcgcaagct gcgcaccttg ttccagtccc ttggctacta cgactcgtcc     360
aaggcatact atgccttcaa ggtctcgttc aacctctgca tctggggctt gtcgactttc     420
attgttgcca gtggggcca gacctcgacc ctcgccaacg tgctctcggc tgcgctcttg     480
ggtctcttct ggcagcagtg cggatggttg gcgcacgact ttttgcacca ccaggtcttc     540
caggaccgtt tctggggtga tcttttcggc gccttcttgg gaggtgtctg ccagggtttc     600
tcgtcctcct ggtggaagga caagcacaac actcaccacg ctgctcccaa cgtccacggc     660
gaggatcccg acattgacac tcaccctctg ttgacctgga gtgagcatgc tctggagatg     720
ttctcggatg ttcctgacga ggagctgacc cgtatgtggt cgcgcttcat ggtcctcaac     780
cagacctggt tctacttccc cattctctcg tttgcccgtc tgtcctggtg cctccagtcc     840
attatgcttg ttctgcccaa cggtcaggcc cacaagccct ctggagcgcg tgtgcccatt     900
tcgttggtcg agcagctgtc tctggctatg cactggacct ggtacctcgc caccatgttc     960
ctgttcatta aggatcccgt caacatgatt gtgtacttt tggtgtcgca ggctgtttgc    1020
ggcaacttgt tggcgattgt gttctcgctc aaccacaacg gcatgcctgt gatctccaag    1080
gaggaagcgg tcgatatgga cttcttcacc aagcagatca tcacgggtcg tgatgttcac    1140
cctggtctgt ttgccaactg gttcacgggt ggattgaact accagattga gcaccacttg    1200
ttcccttcga tgccccgcca caacttttca aagatccagc tgctgtcga ctttgtgc      1260
aaaaagtacg gtgtccgata ccataccact ggtatgatcg agggaactgc agaggtcttt    1320
agccgtttga cgaggtctc caaggcggcc tccaagatgg gcaaggcaca gtaa           1374
```

<210> SEQ ID NO 23
<211> LENGTH: 1341
<212> TYPE: DNA
<213> ORGANISM: Mortierella alpina

<400> SEQUENCE: 23

```
atgggtgcgg acacaggaaa aaccttcacc tggcaagaac tcgcggcgca taacaccgag      60
gacagcctcc ttttggctat ccgtggcaat gtatacgatg tcacaaagtt cttgagccgt     120
catcctggtg aacggatac tctcttgctc ggagctggcc gagatgtcac tccggttttt     180
gagatgtacc acgagtttgg agctgcagag gctatcatga agaagtacta tgttggcaca     240
ctggtctcaa atgagttgcc catcttccca gagccaacgg tgttccataa gaccatcaag     300
ggcagagttg aggcatactt taaggaccgg aacatggatt ccaagaacag accagagatc     360
tgggggacgat atgctctcat ctttggatcc ttgatcgcct cttactacgc gcagctcttt     420
gtaccgttcg tggtcgaacg tacatggctc caggtggtgt ttgctatcat catgggattt     480
gcgtgcgcgc aagtcggatt gaaccctctt cacgatgcct cccacttttc agtgacccac     540
```

```
aaccccaccg tttggaagat tctcggagcc acgcacgact ttttcaacgg agcatcgtat    600
ctcgtgtgga tgtaccaaca tatgctcggc catcatccct ataccaacat tgctggagct    660
gatcccgatg tgtcgacctc tgagcccgat gttcgtcgta tcaagcccaa ccaaaagtgg    720
ttcgtcaacc acatcaacca gcacatgttt gttccttttcc tgtacggact gctggcgttc    780
aaggtgcgca tccaggacat caacatcttg tactttgtca agaccaatga cgccattcgt    840 gtcaaccccca tctcgacttg gcacaccgtc atgttctggg gcggaaaggc cttcttttgtc    900 tggtaccgct tgatcgttcc tatgcagtat ctgcccctga gcaaggtgtt gctcttgttt    960
accgtcgcag acatggtctc ttcttactgg ctggcgctga ccttccaggc gaaccacgtt   1020
gttgaggagg ttcagtggcc attgcctgat gagaatggaa tcatccaaaa ggattgggca   1080
gccatgcagg tcgagactac tcaggattac gcccacgatt cgcacctctg gaccagcatc   1140
acgggcagct tgaactacca agccgttcat catctgttcc cgaacgtttc ccagcatcac   1200
taccctgata tcctggctat catcaaggac acctgcagcg agtacaaggt gccataccctc   1260 gtcaaggata ccttttggca agcgtttgct tcacatttgg agcacttgcg tgtgcttggt   1320
cttcgtccca aggaagagta a                                            1341

<210> SEQ ID NO 24
<211> LENGTH: 1341
<212> TYPE: DNA
<213> ORGANISM: Mortierella alpina

<400> SEQUENCE: 24
atgggtgcgg acacaggaaa aaccttcacc tggcaagaac tcgcggcgca taacaccgag     60
gacagcctcc ttttggctat ccgtggcaat gtatacgatg tcacaaagtt cttgagccgt    120
catcctggtg gaacggatac tctcttgctc ggagctggcc gagatgtcac tccggttttt    180
gagatgtacc acgagtttgg agctgcagag gctatcatga agaagtacta tgttggcaca    240
ctggtctcaa atgagttgcc catcttccca gagccaacgg tgttccataa gaccatcaag    300
ggcagagttg aggcatactt taaggaccgg aacatggatt ccaagaacag accagagatc    360
tggggacgat atgctctcat cttttggatcc ttgatcgcct cttactacgc gcagctcttt    420
gtaccgttcg tggtcgaacg tacatggctc caggtggtgt ttgctatcat catgggattt    480
gcgtgcgcgc aagtcggatt gaaccctctt cacgatgcct cccactttc agtgacccac    540 aaccccaccg tttggaagat tctcggagcc acgcacgact ttttcaacgg agcatcgtat    600
ctcgtgtgga tgtaccaaca tatgctcggc catcatccct ataccaacat tgctggagct    660
gatcccgatg tgtcgacctc tgagcccgat gttcgtcgta tcaagcccaa ccaaaagtgg    720
ttcgtcaacc acatcaacca gcacatgttt gttccttttcc tgtacggact gctggcgttc    780
aaggtgcgca tccaggacat caacatcttg tactttgtca agaccaatga cgccattcgt    840 gtcaaccccca tctcgacttg gcacaccgtc atgttctggg gcggaaaggc cttcttttgtc    900 tggtaccgct tgatcgttcc tatgcagtat ctgcccctga gcaaggtgtt gctcttgttt    960
accgtcgcag acatggtctc ttcttactgg ctggcgctga ccttccaggc gaaccacgtt   1020
gttgaggagg ttcagtggcc attgcctgat gagaatggaa tcatccaaaa ggattgggca   1080
gccatgcagg tcgagactac tcaggattac gcccacgatt cgcacctctg gaccagcatc   1140
acgggcagct tgaactacca agccgttcat catctgttcc cgaacgtttc ccagcatcac   1200
taccctgata tcctggctat catcaaggac acctgcagcg agtacaaggt gccataccctc   1260 gtcaaggata ccttttggca agcgtttgct tcacatttgg agcacttgcg tgtgcttggt   1320
```

```
cttcgtccca aggaagagta a                                              1341

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cacaccacac attcaacatc                                                  20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccttcgtcc ttggtacacc ttgac                                            25

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcggctcggt cccaagatga ac                                               22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcgtctgtca tgtgcccagt ca                                               22

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tttttttttt tttttttttt tttttttttt                                       30

<210> SEQ ID NO 30
<211> LENGTH: 1254
<212> TYPE: DNA
<213> ORGANISM: Mortierella alpina

<400> SEQUENCE: 30
atggatgaat ccaccaccac cacccaccac acagagacca gcagcaagac gtcctcgcac       60
ccccgtcggc tcggtcccaa gatgaacccc atctacaagg gtctgcgagc ctttgtctgg      120
```

-continued

| | |
|---|---|
| gccttgtact tcaacctagg agcatctctc atatcgataa cccaagtcct gtcgttgcct | 180 |
| ctggcgttga tcgctccaaa agtttaccag tggcacatca ctaaaaccca gggtcacttt | 240 |
| ggggctttcc tgctcaagat gaaccagcta tttgcgccct cagatatcgt cttgacggga | 300 |
| gatgaaagtg tcaggggaat cgtcaaggta taccaaggac gaaggctgaa ggacactggt | 360 |
| gaggcgtaca gcggtcatgg agaggacatt attctggata tgcccgagag gatggttttc | 420 |
| atcgcgaacc accagatcta ttctgactgg atgtacctct ggtgcttctc ctatttcgca | 480 |
| gagaggcaca gggcactgaa gattattctt cggggcgacc tgacctggat ccctgtcttt | 540 |
| ggctggggta tgcggttctt tgactttatc tttttgaaac gtaatgactg gcacatgac | 600 |
| agacgcgcca ttgaggagaa cctgggacgt gtcaaggaaa aggatccact ctggctggta | 660 |
| gtcttccctg aaggaacagt cgtctccaag gaaacgcgtt tgcgatctgt tgccttttca | 720 |
| aagaaggctg gtcttcgga tcaccgccat gtgttgcttc caagaaccag cggcctcttt | 780 |
| gtttgcatca acaagttgcg tggatccgtc gaatacttat acgacgcgac agttggctac | 840 |
| tcgaacgttg aatatggaga gattccacag gagctttacc ctttgccagg gctatatatc | 900 |
| aacaaggcgc agcccaagga gatcaacatg cacctgcggc ggtttgctat caaggatatc | 960 |
| cccacgtcag aacccgagtt tgtggagtgg gtccgagcgc ggtgggtaga aaggatgag | 1020 |
| ctgatggagt agttttatac caagggccga ttcccatcgc agctgacggc tgaggacatt | 1080 |
| ggcgagaagg agaccaacaa ggcaggaggc tcatctgaag acagagtgt cagaatcccg | 1140 |
| ctcaaatcgc gaggcatgat ggactacctc atgccttcgg ccattaacct ggttgcgctg | 1200 |
| ccagtactgg ctttgcgat gagatatgct ctgcagcaag tatcgtctgg ttga | 1254 |

<210> SEQ ID NO 31
<211> LENGTH: 1254
<212> TYPE: DNA
<213> ORGANISM: Mortierella alpina

<400> SEQUENCE: 31

| | |
|---|---|
| atggatgaat ccaccacgac caccacgcac cactcagaga ccagcagcaa gacgtcctcg | 60 |
| caccccccgcc ggctcggtcc cgagatgaac cctatctaca agggtctgcg agccattgtc | 120 |
| tgggcctttt acttcaacct gggagcgtcg cttatatcga tcacgcaggt gctgtcgctg | 180 |
| cctctggcgt tgattgctcc aggggtctac cagtggcaca tcagcaaaac acagggtcac | 240 |
| tttggagctt tcctgctccg gatgaaccag ctctttgcgc cgtcagatat tgtcttgaca | 300 |
| ggggacgaga gtgtcagggg aatcgtcaag gtctacaaag gacggaacct gaaggaggcc | 360 |
| ggtgagccag gcagcggtca gggagaggac attcttctgg atatgcccga ggatggtt | 420 |
| tcattgcga accaccagat ctactctgac tggatgtacc tctggtgctt ctcctatttt | 480 |
| gcagagaggc acagggcact gaagattatt cttcggggcg acctgacctg gatccctgtc | 540 |
| tttgctggg gtatgcggtt ctttgacttt atctttttga acgtaatga ctgggcacac | 600 |
| gatcgccgtg ccattgagga aaacttggga cgtgtcaagg aaaaggatcc cctctggctc | 660 |
| gtggtcttcc ccgagggaac agtcgtctcc aaggaaacgc gtctccgatc cgttgccttt | 720 |
| tcaaagaagg ctagtctgtc ggatcaccgc catgtgctgc ttccaaggac cagcggtctg | 780 |
| tttgtgtgca tcaacaagtt gcgtggatct gtcgactact gtacgatgc aaccgttggc | 840 |
| tactcgaatg tcgagtatgg cgagattccg caggagcttt acccgttacc aggactgtat | 900 |
| atcaacaaag cacagcccaa ggagatcaac atgcacctgc gtcgatttgc gatcaaggat | 960 |
| atccccacgt cagaacccga atttgtggaa tgggtccgag ctcggtgggt ggagaaggat | 1020 |

-continued

```
gagttgatgg aagagtttta taccaagggc cgatttccat cacaactgac ggccgccgac    1080
attggtgaga aggaggtcaa gacggcagga ggtccaacgg agggacagag tgtcaggatc    1140
ccgctcaagg cgcgaggcat gatggactac ctcatgccct cggtcatgaa tctgatcgcc    1200
cttcctgtgc tggcgtttgc gatgagatat gcagtgcagc aagcatcggg ctga          1254
```

<210> SEQ ID NO 32
<211> LENGTH: 417
<212> TYPE: PRT
<213> ORGANISM: Mortierella alpina

<400> SEQUENCE: 32

```
Met Asp Glu Ser Thr Thr Thr Thr His His Ser Glu Thr Ser Ser
1               5                   10                  15

Lys Thr Ser Ser His Pro Arg Arg Leu Gly Pro Glu Met Asn Pro Ile
            20                  25                  30

Tyr Lys Gly Leu Arg Ala Ile Val Trp Ala Phe Tyr Phe Asn Leu Gly
        35                  40                  45

Ala Ser Leu Ile Ser Ile Thr Gln Val Leu Ser Leu Pro Leu Ala Leu
    50                  55                  60

Ile Ala Pro Gly Val Tyr Gln Trp His Ile Ser Lys Thr Gln Gly His
65                  70                  75                  80

Phe Gly Ala Phe Leu Leu Arg Met Asn Gln Leu Phe Ala Pro Ser Asp
                85                  90                  95

Ile Val Leu Thr Gly Asp Glu Ser Val Arg Gly Ile Val Lys Val Tyr
            100                 105                 110

Lys Gly Arg Asn Leu Lys Glu Ala Gly Glu Pro Gly Ser Gly Gln Gly
        115                 120                 125

Glu Asp Ile Leu Leu Asp Met Pro Glu Arg Met Val Phe Ile Ala Asn
    130                 135                 140

His Gln Ile Tyr Ser Asp Trp Met Tyr Leu Trp Cys Phe Ser Tyr Phe
145                 150                 155                 160

Ala Glu Arg His Arg Ala Leu Lys Ile Ile Leu Arg Gly Asp Leu Thr
                165                 170                 175

Trp Ile Pro Val Phe Gly Trp Gly Met Arg Phe Phe Asp Phe Ile Phe
            180                 185                 190

Leu Lys Arg Asn Asp Trp Ala His Asp Arg Arg Ala Ile Glu Glu Asn
        195                 200                 205

Leu Gly Arg Val Lys Glu Lys Asp Pro Leu Trp Leu Val Val Phe Pro
    210                 215                 220

Glu Gly Thr Val Val Ser Lys Glu Thr Arg Leu Arg Ser Val Ala Phe
225                 230                 235                 240

Ser Lys Lys Ala Ser Leu Ser Asp His Arg His Val Leu Leu Pro Arg
                245                 250                 255

Thr Ser Gly Leu Phe Val Cys Ile Asn Lys Leu Arg Gly Ser Val Asp
            260                 265                 270

Tyr Leu Tyr Asp Ala Thr Val Gly Tyr Ser Asn Val Glu Tyr Gly Glu
        275                 280                 285

Ile Pro Gln Glu Leu Tyr Pro Leu Pro Gly Leu Tyr Ile Asn Lys Ala
    290                 295                 300

Gln Pro Lys Glu Ile Asn Met His Leu Arg Arg Phe Ala Ile Lys Asp
305                 310                 315                 320

Ile Pro Thr Ser Glu Pro Glu Phe Val Glu Trp Val Arg Ala Arg Trp
                325                 330                 335

Val Glu Lys Asp Glu Leu Met Glu Glu Phe Tyr Thr Lys Gly Arg Phe
```

-continued

```
                    340                 345                 350
Pro Ser Gln Leu Thr Ala Ala Asp Ile Gly Glu Lys Glu Val Lys Thr
        355                 360                 365

Ala Gly Gly Pro Thr Glu Gly Gln Ser Val Arg Ile Pro Leu Lys Ala
    370                 375                 380

Arg Gly Met Met Asp Tyr Leu Met Pro Ser Val Met Asn Leu Ile Ala
385                 390                 395                 400

Leu Pro Val Leu Ala Phe Ala Met Arg Tyr Ala Val Gln Gln Ala Ser
            405                 410                 415

Gly
```